(12) United States Patent
Sarpeshkar et al.

(10) Patent No.: US 8,242,429 B2
(45) Date of Patent: Aug. 14, 2012

(54) ULTRA-LOW-POWER PULSE OXIMETER IMPLEMENTED WITH AN ENERGY-EFFICIENT PHOTORECEPTOR

(75) Inventors: Rahul Sarpeshkar, Arlington, MA (US); Maziar Tavakoli Dastjerdi, Waltham, MA (US)

(73) Assignee: Rahul Sarpeshkar, Arlington, MA (US)

( * ) Notice: Subject to any disclaimer, the term of this patent is extended or adjusted under 35 U.S.C. 154(b) by 1359 days.

(21) Appl. No.: 11/903,571

(22) Filed: Sep. 24, 2007

(65) Prior Publication Data

US 2009/0163784 A1 Jun. 25, 2009

Related U.S. Application Data

(60) Provisional application No. 60/847,034, filed on Sep. 25, 2006.

(51) Int. Cl.
*H03F 3/08* (2006.01)
*H01J 40/14* (2006.01)
(52) U.S. Cl. ................. 250/214 A; 250/214 R; 330/308
(58) Field of Classification Search ............... 250/214 A, 250/214 R, 214 AL, 214 LA, 214 AG, 214 L, 250/214 SW, 214 C, 214.1; 330/85, 98–100, 254, 260, 265, 271, 308
See application file for complete search history.

(56) References Cited

U.S. PATENT DOCUMENTS

| | | | |
|---|---|---|---|
| 4,773,422 A | 9/1988 | Isaacson et al. | |
| 5,311,353 A | * 5/1994 | Crawford | 359/333 |
| 6,360,113 B1 | 3/2002 | Dettling | |

* cited by examiner

*Primary Examiner* — Que T Le
*Assistant Examiner* — Don Williams
(74) *Attorney, Agent, or Firm* — Edwards Wildman Palmer LLP; Barry Kramer

(57) ABSTRACT

An energy-efficient photoreceptor apparatus and a transimpedance amplifier apparatus having high energy-efficiency and low power consumption of which are achieved through multiple distributed gain amplification stages, adaptive loop gain control circuitry and unilateralization, thereby enabling fast and precise performance over a wide range of input-current levels. The high-energy efficiency, robust feedback stability and performance of the present invention can be utilized to achieve sub-milliwatt pulse oximeters and may be employed in other current-to-voltage amplification and conversion applications. The use of analog processing on the outputs of the photoreceptor apparatus also helps lower the overall power of pulse oximeters.

53 Claims, 14 Drawing Sheets

ULTRA-LOW-POWER PULSE OXIMETER IMPLEMENTED WITH AN ENERGY-EFFICIENT PHOTORECEPTOR

CROSS-REFERENCE TO RELATED APPLICATIONS

This application is based upon and claims the benefit of priority under 35 U.S.C. § 119(e) from U.S. Provisional Patent Application No. 60/847,034, filed Sep. 25, 2006, the entire contents of which are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of N00014-02-1-0434 awarded by the Office of Naval Research.

BACKGROUND OF THE INVENTION

A. Field of the Invention

The present invention relates to energy-efficient photoreceptors, which are constructed with an ultra-low-power transimpedance amplifier apparatus and photodiode in a pulse oximeter application. The energy-efficient photoreceptor apparatus and transimpedance amplifier apparatus disclosed herein provide increased sensitivity, dynamic range, speed, and energy efficiency relative to known photoreceptor devices and allow for a significant reduction of power consumption requirements. In addition, the use of analog processing after the photoreceptor also lowers power consumption.

B. Description of the Related Art

Pulse oximetry is a fast, noninvasive, easy-to-use, and continuous method for monitoring the saturation of components such as oxygen or carbon monoxide in the blood of an organism such as an animal, non-human primate or human patient. Pulse oximeters for blood-oxygen saturation detection operate by comparing transmission characteristics of red and infrared light emitting diodes (LEDs) light through a patient's finger with a photoreceptor. The wavelength and strength of the light that passes through the finger provides information on what proportion of the hemoglobin in the blood is dark red and deoxygenated versus bright red and oxygenated. The modulation of the oximeter signal with arterial diameter due to blood pressure variations in between heartbeats helps separate blood transmission characteristics from the unmodulated tissue background.

A pulse oximeter having a photoreceptor is ubiquitous in modern medicine for non-invasively measuring the percentage of oxygenated hemoglobin in a patient's blood, by comparing transmission characteristics of red and infrared LED light, through their fingers with a photoreceptor. In modern medical practice, a patient's blood-oxygen level is considered one of the important vital signs of the body along with the more traditional ones, such as blood pressure, heart rate, body temperature, and breathing rate. Pulse oximeters provide early information on problems in both the respiratory and circulatory systems. They are widely used in intensive care, operating rooms, emergency care, birth and delivery, neonatal and pediatric care, sleep studies, and in veterinary care.

The most frequent use of pulse oximeters is in the field of anesthesiology. Tissue oxygenation and, consequently, blood saturation are of extreme importance to anesthesiologists because they administer narcotics to the patient to suppress the central nervous system. This administration stops the patient's desire to breathe and places her in a state where she can no longer meet oxygen demands on her own. In addition, anesthesiologists administer muscle relaxants, which stop the ability to breathe and permit airways to collapse. Thus, it is necessary to restore breathing through intubation and artificial respiration. In a sense, the anesthetist becomes the controller for the patient's respiratory system, and the blood-oxygen level provides the best feedback variable.

In an additional to blood-oxygen level detection, detection of carbon monoxide is also increasingly desired. Carbon monoxide is a tasteless, odorless, invisible gas that can build up in enclosed areas where fuels such as natural gas, gasoline, fuel oil, or wood are burned. When an organism inhales carbon monoxide, it begins to replace the oxygen that is normally carried in the blood, which leads to carbon monoxide poisoning. Carbon monoxide poisoning can cause headaches, dizziness, or nausea in humans. If the exposure to carbon monoxide continues, a person may lose consciousness and even die. Carbon monoxide poisoning can be hard to identify. The symptoms can also be caused by several other illnesses. Treatment for carbon monoxide poisoning involves bringing blood oxygen levels back to normal. It is important that an affected person or animal be removed from the area where carbon monoxide may be present and begin oxygen therapy if needed. In the context of carbon monoxide detection, a corresponding apparatus can be used to detect the saturation of carboxyhemoglobin and methemoglobin which are indicative of carbon monoxide poisoning in an organism's blood. Here, the received photocurrent consists of light of multiple wavelengths, rather than only two wavelengths as in oxygen saturation detection. However, like blood-oxygen detection, the light is received from the specimen, transduced from a photocurrent to a stream of electrons, and amplified in order to determine saturation, as in pulse oximetry.

In addition to the applications discussed above, there is a growing demand today for small, low-power, and cheap pulse oximeters and carbon monoxide detectors suitable for many novel and exciting portable, wearable, wireless, and networked medical applications where power consumption needs to be minimal, and real-time detection is important. For instance, home-care monitoring for elderly or chronically ill patients over the Internet is gaining popularity as a continuous and flexible alternative to costly medical supervision in hospitals and nursing homes. Moreover, the military is seeking solutions to remotely monitor the health of soldiers in the battlefield by using light and durable sensor tags attached to their bodies along with radio transceivers to enable wireless monitoring. Other potential applications for such cheap and portable biomedical sensors will also include athlete or farm animal monitoring, emergency patient transport, and wireless sensor networks. Reducing the power consumption of such sensors is a critical step in such applications as power directly dictates battery life, size, and cost which in turn influence the dimensions and price of the overall device. The explosion of wireless networks having a transceiver device such as Bluetooth, 802.11a, 802.11b, 802.11g, Zigbee (802.15.4), and cellular telephones in today's world has increased the appetite for having medical information constantly available via devices wirelessly connected to the internet and or to secure data bases in hospitals.

One known pulse oximeter is disclosed in U.S. Pat. No. 4,773,422 (the '422 patent) to Isaacson, et al. The '422 patent discloses an electronic apparatus for sensing the percentage of constituents in arterial blood and employs a logarithmic amplifier built with bipolar transistors and means for subtracting ambient light signals. However, the '422 patent does not teach or suggest the benefits of low-power consumption and energy efficiency that the present invention provides. These mechanisms include: distributed gain amplification, adaptive loop gain control and unilateralization employed in a transimpedance amplifier apparatus and energy-efficient photoreceptor apparatus, the use of MOS transistors operated in the subthreshold regime to implement a logarithm on standard microelectronic chips, the use of analog processing to lower power consumption, and other benefits described below.

SUMMARY OF THE INVENTION

The present invention provides a transimpedance amplifier apparatus and an energy-efficient photoreceptor apparatus for use in a pulse-oximeter system. The apparatuses disclosed herein dissipate significantly less power compared to the best low-power commercial pulse oximeters in the related art. LED power consumption, which normally dominates the power requirement of pulse oximeters, is reduced in the present invention because of the novel photoreceptor or transimpedance amplifier and photodiode. The transimpedance amplifier transduces received light into electrons and is employed at the front-end of the photoreceptor circuitry, which is fast, precise and ultra-low-power compared with prior designs and operates over a wide range of light levels. Moreover, in contrast to traditional analog to digital conversion and digital signal processing approaches, the present invention performs all required signal processing in the analog domain and eliminates the need for digital signal processing completely, leading to a very area-efficient single-chip system.

In accordance with the present invention, a transimpedance amplifier apparatus and an energy-efficient photoreceptor apparatus are disclosed. Each has distributed gain amplification, adaptive loop gain control and unilateralization means and capabilities. In an exemplary application, the photoreceptor of the present invention is employed in an analog single-chip pulse oximeter system with 4.8 mW total power dissipation, an order of magnitude below state-of-the-art commercial implementations whose dissipation is estimated near 55 mW.

The majority of this power reduction is due to the use of a novel photoreceptor, i.e., transimpedance amplifier plus photodiode, with inherent contrast sensitivity, distributed amplification, unilateralization, and adaptive loop gain control. The enhanced sensitivity and improved power efficiency of the photoreceptor to the signal of interest allows LED power to be significantly reduced. The direct result of the power-efficiency is that while batteries in a commercial oximeter need replacement every five days, the analog pulse oximeter of the present invention allows for two months of operation. Therefore, the present invention is well suited for portable medical applications such as continuous home-care monitoring for elderly or chronic patients, emergency patient transport, remote soldier monitoring, wireless medical sensing such that transmission of blood-oxygen or carbon monoxide saturation can be obtained at a remote or central location. The design of the present invention obviates the need for analog to digital and digital signal processing and leads to a small single-chip solution for providing pulse oximeters with power consumption in the sub-milliwatt range. The output-voltage signal can be further connected to a display unit for displaying information about the saturation of either oxygen or carbon monoxide in an organism.

The foregoing objects, features, and advantages of the invention will become clearer to those skilled in the art from the following detailed description, especially considered in conjunction with the accompanying drawings.

DETAILED DESCRIPTION OF AN EXEMPLARY EMBODIMENT

I. Basic Principles of Pulse Oximetry

Figure 1:
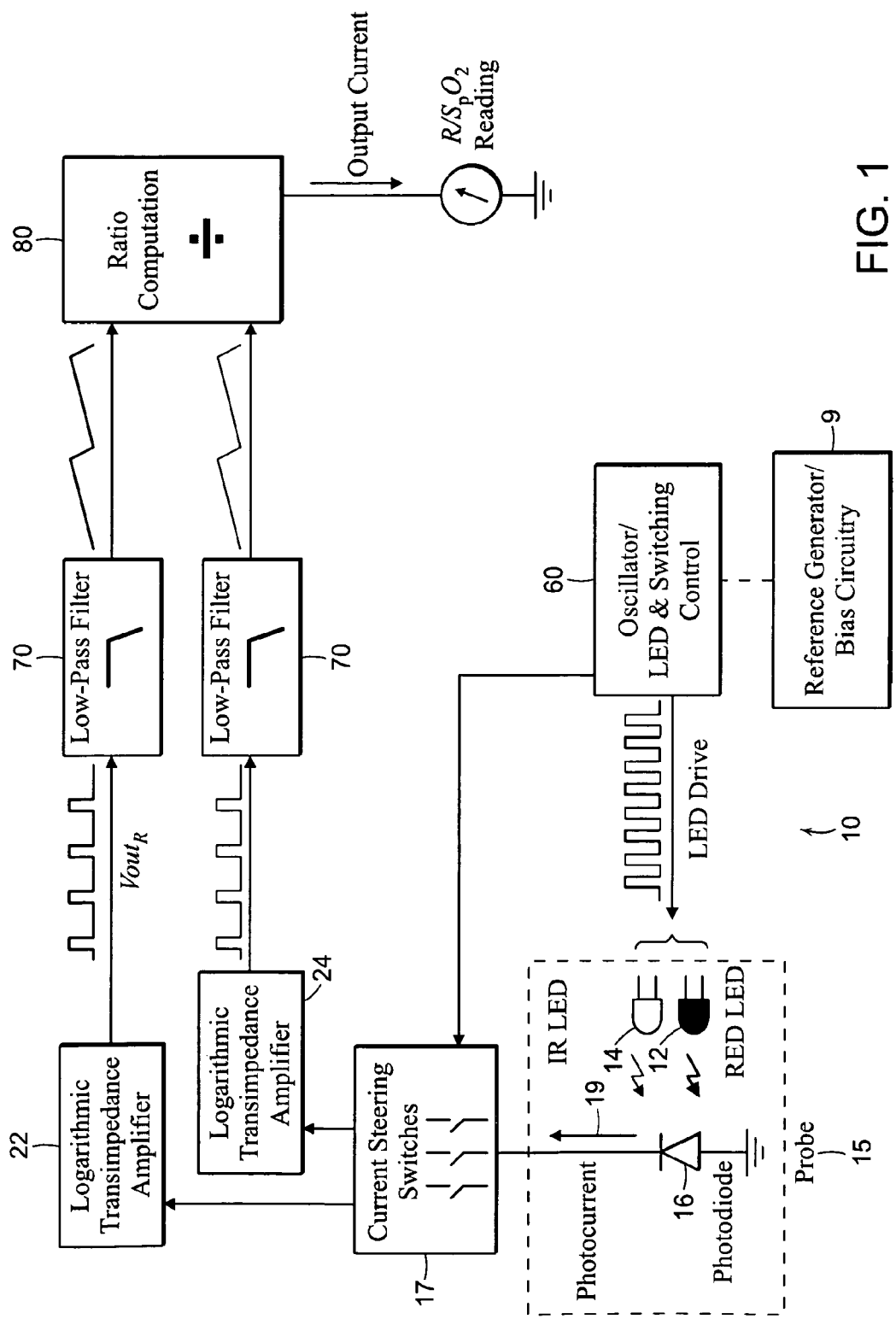
FIG. 1 illustrates the structure of the energy-efficient photoreceptor apparatus employed in a pulse oximeter system according to the present invention.

The basic concept underlying operation of pulse oximeters is that hemoglobin changes color from dark red to bright red when oxygenated and reduces its absorption of red light. Hence, if red LED light at 660 nm is shone through one side of a patient's finger and the transmitted light is measured on the other side of the patient's finger with a photoreceptor, the oxygen saturation, $S_pO_2$, i.e., the percentage of hemoglobin molecules that are oxygenated in the blood of the patient's finger, can be determined. However, other tissues like skin and bone which surround the arteries and veins that carry blood will affect the absolute measurement. Fortunately, arteries dilate and contract with each heartbeat such that during systole, the phase in which the ventricles of the heart contract and the blood pressure rises, relatively thicker arteries increase absorption of light. During diastole, the phase in which the ventricles of the heart relax and blood pressure falls, relatively thinner arteries decrease absorption of light. Thus, by taking the ratio of the light measured by the photoreceptor at the peak and trough of a heartbeat cycle, information that is independent of the absolute light intensity of the LED and independent of tissues that do not contain arterial blood, e.g., veins, skin, and bone, which do not modulate their absorption with heartbeat cycles, can be obtained. This ratio is still exponentially dependent on the absolute concentration of hemoglobin molecules in the blood (oxygenated or deoxygenated), the absorption coefficient of red light by hemoglobin, and on the thickness variation of the arteries over a heartbeat cycle.

To avoid exponential dependency on these unknowns, the logarithm of the peak-to-trough ratio can be computed. If another logarithmic peak-to-trough ratio measurement with a 940 nm infrared LED is made, and the ratio of the two ratio measurements is taken, any dependence on the absolute concentration of hemoglobin and on the thickness variation of arteries over a heartbeat cycle disappears in the final ratio as these unknowns are the same for both measurements and cancel in the final ratio. The final ratio provides information that is dependent only on the absorption coefficients of deoxygenated and oxygenated hemoglobin and on the percentage of hemoglobin that is oxygenated, the desired output of the oximeter, $S_pO_2$. Since the absorption coefficients of deoxygenated and oxygenated hemoglobin are well known from other molecular measurements, the percentage of hemoglobin that is oxygenated can be obtained from a simple calculation.

Beer's law describes the attenuation of (monochromatic) light traveling through a medium containing an absorbing substance and predicts it to be an exponential function of the product of three quantities: the distance through the medium, the concentration of the substance, and its intrinsic molecular absorption (extinction) coefficient. It can be shown that the pulse oximeter's desired output is given by $$S_pO_2 = \frac{0.81 - 0.18R}{0.73 + 0.11R} \times 100\% \quad (1)$$

where the constants in (1) are related to the absorption (extinction) coefficients of oxygenated and deoxygenated hemoglobin at 660 nm and at 940 nm. In this equation, R represents a parameter called the "ratio of normalized absorbances." This is the quantity actually measured by pulse oximeters, and is given by $$R = \frac{\ln(I_{L,R}/I_{H,R})}{\ln(I_L, I_{IR}/I_H)} = \frac{i_{ac,R}/I_{DC,R}}{i_{ac,IR}/I_{DC,IR}} \quad (2)$$

The symbols $I_L$, $I_H$, $i_{ac}$ and $I_{DC}$ denote the minimum value, maximum value, ac component, and DC component (average) of the red (R) and infrared (IR) light signals that are modulated by the pulsations of arterial blood and detected at the photoreceptor. The AC component of interest in (2) is the signal component at the heart rate ($f_p$) that is normally around 60-120 beats per minute (bpm) or equivalently 1-2 Hz in a healthy adult. The alternating current/digital current (AC/DC) terms on the right-hand side of (2) are known to be an excellent approximation to the left-hand side of (2) for the small AC signals and large DC signals that are typically found in pulse oximetry applications since $d(\log(U))=(dU/U)$.

Some secondary effects, such as scattering of light in human or animal tissue or its reflection at the surface of the skin, are not accounted for in Beer's law. These physical processes, which are very hard to model in a complex medium such as human or animal body, necessitate empirical calibration of all pulse oximeters. For example, to calibrate commercial pulse oximeters, a large set of data is obtained in clinical studies from large number of subjects. The collected data contains information about R provided by the non-invasive pulse oximeter that is paired with actual $S_pO_2$ readings found by analyzing blood samples of the subjects in a lab. Polynomial equations are then used to find an empirical relationship between R and $S_pO_2$ that has less error than (1).

II. Pulse Oximeter Application

A block diagram of the pulse oximeter system 10 according to the present invention is shown in FIG. 1. The input to the chip is an input-current signal, here a photocurrent 19, coming from the probe and the output of the chip is another current directly proportional to R. The photocurrent obtained can correspond to saturation of either carbon monoxide or oxygen. However, by way of an exemplary embodiment, detection of blood-oxygen levels in the pulse oximetry context is discussed herein.

To save power dissipation in the LEDs 12,14, the LED drive signals are chopped by a square wave with a small duty cycle, and a switching frequency $f_s$ (3% and 100 Hz in setup, respectively in this example) from the oscillator/LED & switching control block 60. The arterial blood pulsations at the heart rate frequency ($f_p$) AM modulate the chopped LED light passing through the tissue. The switching frequency $f_s$ is still much higher than $f_p$ such that aliasing effects are minimal.

The red LED 12 and infrared LED 14 are alternatively illuminated, and the photocurrent 19, generated by a single photodiode 16, is split, switched, and steered into two different paths or channels by current steering switches 17; one channel sensitive to the red light and the other to infrared light. The photocurrent 19 undergoes amplification by the logarithmic transimpedance amplifiers 22,24, low-pass filters (LPF) 70, and a ratio computation block 80.

A. Photoreceptor Structure

Figure 2B:
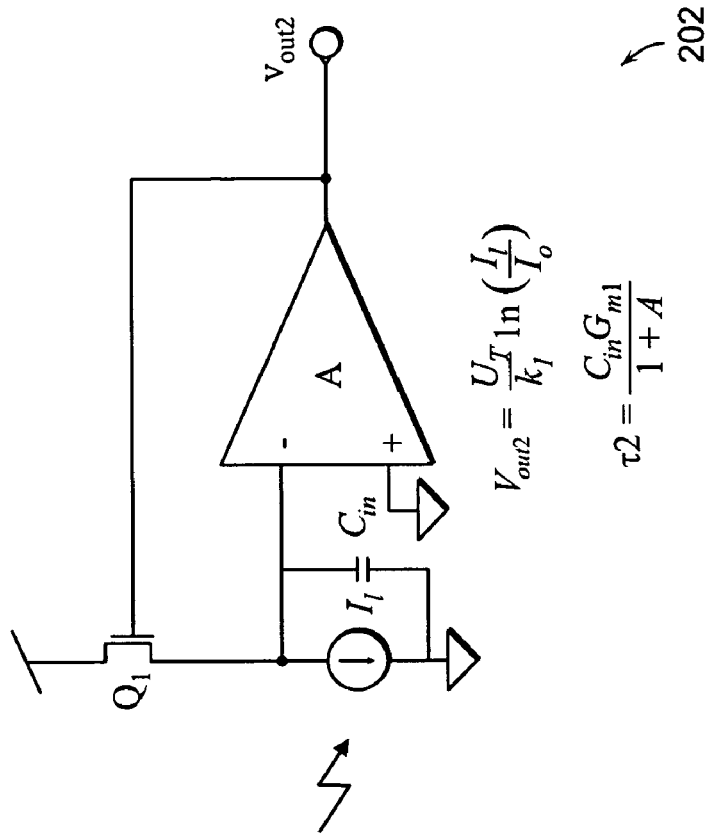
FIG. 2b is a circuit schematic of a known single-stage logarithmic transimpedance amplifier.
Figure 2A:
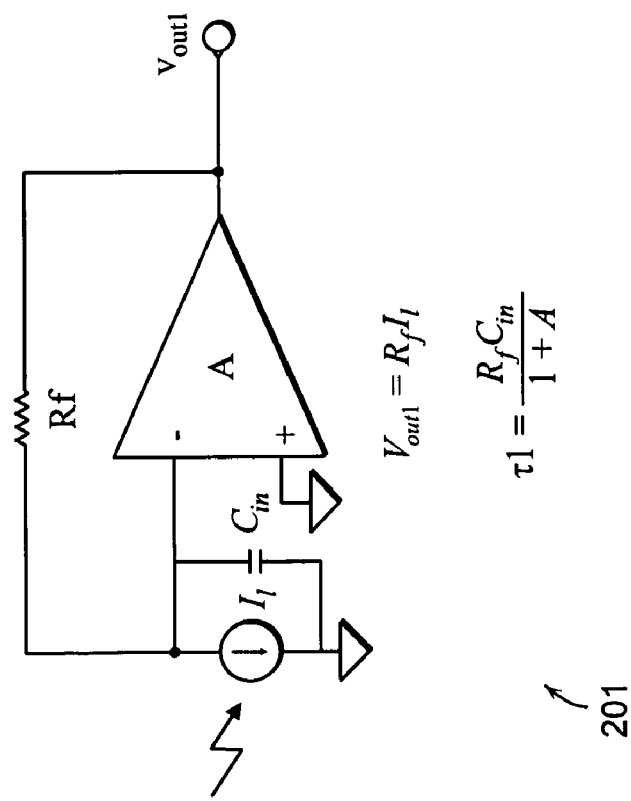
FIG. 2a is a circuit schematic of a known single-stage linear transimpedance amplifier.

Important building blocks of the pulse oximeter system 10 of the present invention are its two front-end transimpedance amplifiers, which convert the light-generated input-current signal to an output-voltage signal. Here, logarithmic transimpedance amplifiers 22, 24 are used in this exemplary embodiment. However, the disclosed pulse oximeter system 10 may also be implemented with a linear amplifier 201, shown in FIG. 2a, which is used in most commercially available pulse oximeters. The amplifier (A) is utilized to attenuate the effect of the typically large parasitic capacitance of the photodiode 16, thus decreasing the time constant, and increasing the bandwidth of the photoreceptor. FIG. 2b shows the circuit schematic of the logarithmic transimpedance amplifiers 22, 24 of FIG. 1, used in an embodiment of a pulse oximeter system 10 of the present invention. The logarithmic characteristic of the transimpedance amplifier is achieved by the feedback transistor $Q_1$. The feedback transistor $Q_1$ operates in its subthreshold regime of operation (since $I_1$ is fairly small) and exhibits an exponential I-V characteristic.

The key incentive behind the employment of a logarithmic instead of a linear transimpedance amplifier is that the logarithmic transimpedance amplifier is inherently sensitive to the AC/DC contrast of the input photocurrent signal since the derivative of a log(U) function is equal to the derivative of U over U itself. If the logarithmic large-signal relationship between $I_1$ and $V_{out2}$ shown in the circuit of FIG. 2b is Taylor expanded to find its small-signal output-voltage, the AC voltage out obtained can be described by $$V_{ac,out2} = \left(\frac{dV_{out2}}{dI_1}\right)i_{ac,1} = \left(\frac{U_T}{K} \times \frac{\Delta I_o}{I_1}\right)i_{ac,1} = \left(\frac{U_T}{K}\right)\frac{i_{ac,1}}{I_{DC,1}} \quad (3)$$

This voltage is proportional to the AC/DC of the input-current as expected; κ the subthreshold exponential coefficient of $Q_1$ and $U_T$=kT/q is the thermal voltage. Logarithmic transimpedance amplifiers are therefore a perfect fit to oximetry applications. Comparing (2) and (3) reveals that the outputs of the logarithmic transimpedance amplifiers 22, 24 seen in FIG. 1 are automatically proportional to the numerator ($i_{ac,R}/I_{DC,R}$) and the denominator ($i_{ac,IR}/I_{DC,IR}$) of (2), respectively. Therefore, the exploitation of logarithmic computation saves us the need to explicitly calculate two AC and two DC components and then perform two divisions as in conventional linear systems.

Distributed gain amplification, adaptive loop gain control and unilateralization are provided by the present invention in the context of a logarithmic transimpedance amplifier. However, these improvements can also be used to enhance the performance of linear transimpedance amplifiers and thus should not be viewed as specific to the exemplary logarithmic implementation described herein.

Figure 3:
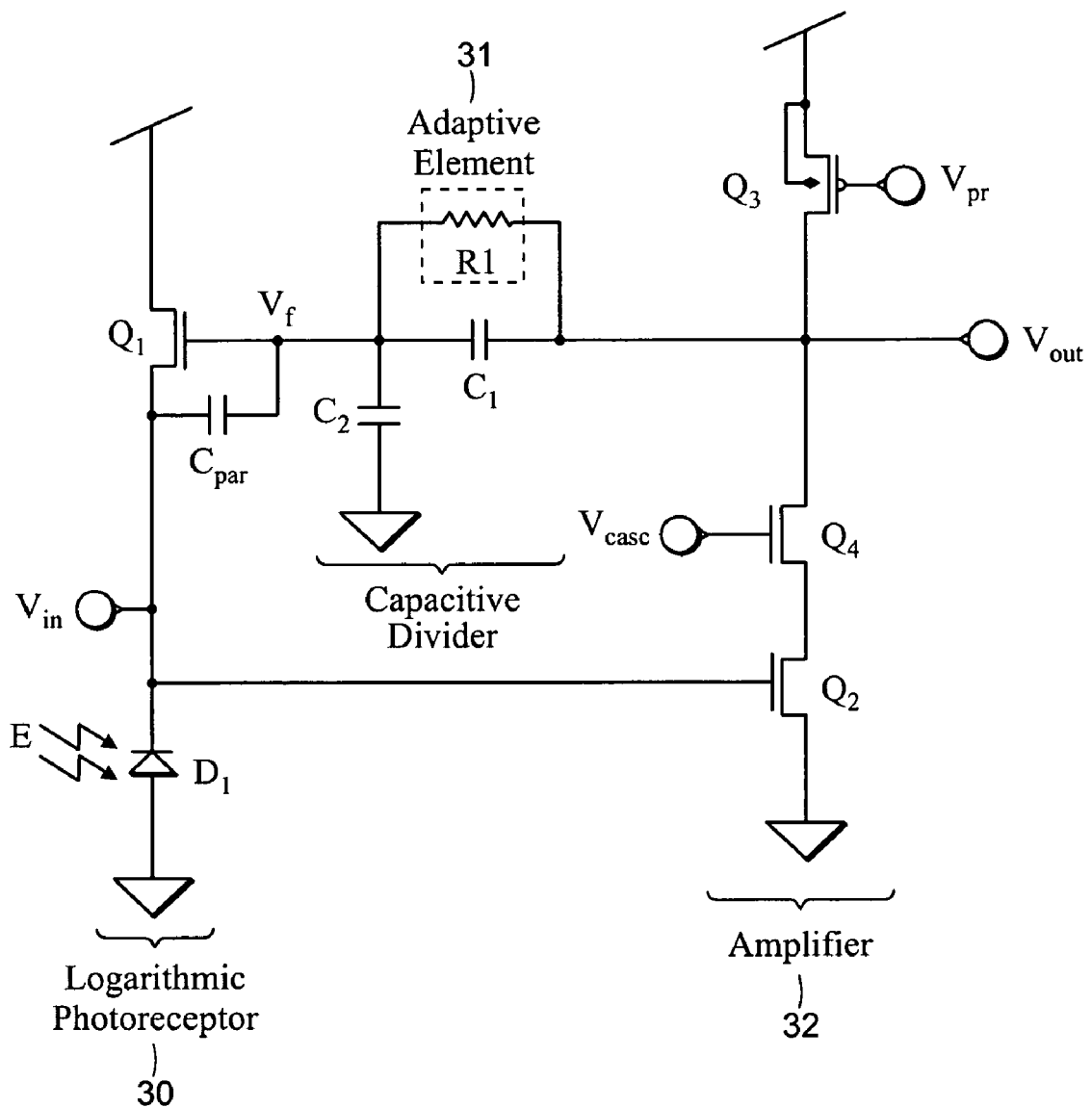
FIG. 3 is a circuit schematic of a known logarithmic photoreceptor with a single-stage amplifier and adaptive temporal filtering.

The circuit schematic of a well-known logarithmic photoreceptor 30 with a single-stage amplifier 31 and adaptive element 32 for temporal filtering is shown in FIG. 3. The properties of this logarithmic photoreceptor include higher AC gain than DC gain, a contrast response, and a relatively wide dynamic range of operation. The diode $D_1$ and transistor $Q_1$ form a logarithmic photoreceptor and transistors $Q_2$-$Q_4$ implement a single-stage inverting common-source logarithmic transimpedance amplifier 202, as shown in FIG. 2B. The elements $C_1$, $C_2$, and $R_1$ in FIG. 3 form a temporal low-pass (LP) filter in the feedback path, which results in an overall high-pass (HP) characteristic for the photoreceptor and boosts the gain for AC signals beyond the HP pole frequency. The use of an adaptive sinh element to realize $R_1$ results in a value around 0.1 Hz for this frequency. The output-voltage of the photoreceptor 30 for AC signals is equal to $$V_{ac,out} = \left(\frac{U_T}{K_1}\right)\left(\frac{C_1 + C_2}{C_1}\right)\frac{i_{ac,1}}{I_{DC,1}} \quad (4)$$

While the logarithmic photoreceptor 30 of FIG. 3 works well for many applications, the limited gain of the simple amplifier and unwanted capacitances in its architecture (i.e. $C_{par}$) limit the speedup of its light-dependent slow input time constant and restrict its closed-loop bandwidth. Furthermore, the bandwidth of the photoreceptor 30 changes linearly with light intensity, an undesirable property if it is to have a performance invariant with LEDs of varying intensities, in fingers of different thickness, and with different skin pigmentation.

Figure 4:
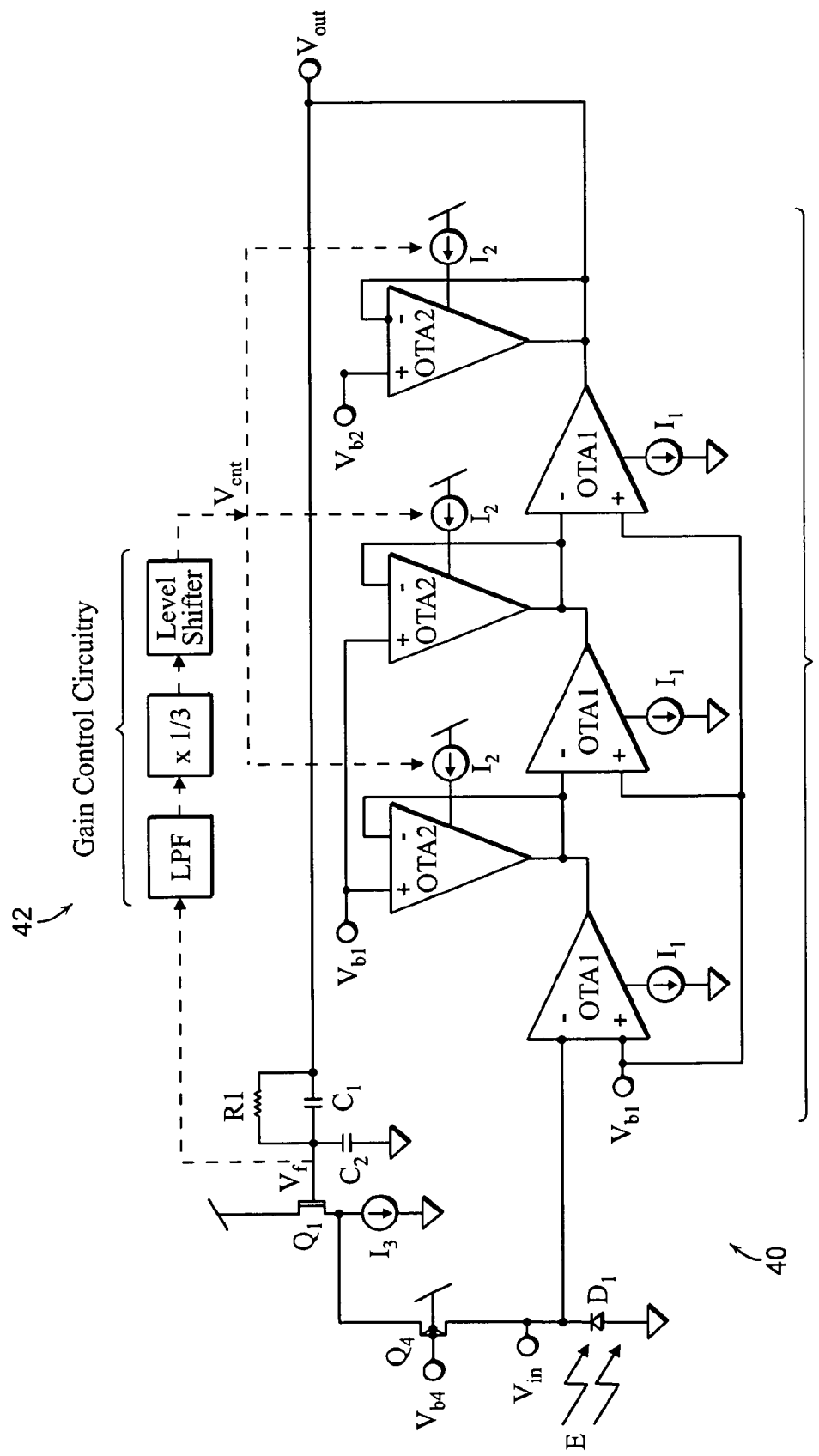
FIG. 4 is a circuit schematic of the energy-efficient photoreceptor apparatus with distributed amplifier, adaptive loop gain control, and the unilateralization means of the present invention.

FIG. 4 illustrates the circuit schematic of the energy-efficient photoreceptor apparatus 40 with distributed amplifier 41 with adaptive loop gain control circuitry 42. The photoreceptor apparatus 40 of FIG. 4 improves on the known photoreceptor of FIG. 3 in many primary ways. One improvement is to distribute the gain of the distributed amplifier 41 over multiple low gain stages, rather than one stage, to increase its gain-bandwidth product (GBW) for a given power consumption significantly. The exemplary embodiment illustrates a three-stage distributed amplifier 41 design. A high GBW is necessary for attaining large gains in the amplifier 41 and still ensuring that the feedback loop of the photoreceptor apparatus 40 is stable. A higher gain for the amplifier results in a larger speedup for the light-dependent pole at the input of the transimpedance amplifiers 22, 24. Thus, a smaller LED light intensity and smaller power dissipation is achieved in the pulse oximeter 10 application of the present invention for a given target bandwidth. The high bandwidth ensures that the photoreceptors completely turn ON and settle down in the short ON duration of LED pulses, guaranteeing proper conversion, distribution, and processing of the input red and IR photocurrents.

The gain is distributed over multiple low-gain stages because it is otherwise difficult to build a single-stage amplifier, with a large GBW at low power consumption. A cascade of amplifiers has a significantly larger GBW than a single-stage amplifier with the same gain. If the GBW of each amplifying stage is constant, then the time constant for an N-stage amplifier with identical gains per stage is proportional to $N^{1/2}A^{(1/N)}$ versus being proportional to A for the single-stage case (the single stage has the same overall gain A). Intuitively, the higher GBW is attained because, while time constants add in a cascade, gains multiply. Thus, a large GBW is achieved in a multistage amplifier because the gain can be increased more quickly than the bandwidth is lost.

A numerical example helps clarify the dramatic advantages of distributing gain over multiple low-gain stages. Suppose that in the singe-stage logarithmic transimpedance amplifier 202 topology of FIG. 2b, a gain of 8000 is desired in the transimpedance amplifier to speed up a light pole that initially lies at 1 Hz (open loop) in a typical low light-intensity condition and achieve a closed-loop bandwidth as high as possible. A cascading three-stage implementation can be used, each stage having a gain of twenty. Assuming that each amplifying stage has a GBW of $2\times10^6$ (in Hz), the feedback loop has one open-loop light pole at 1 Hz, three open-loop amplifier poles at $2\times10^6/20=100$ kHz, and a loop gain of 8000. Root locus and feedback loop analysis show that when the loop is closed, the light pole moves to 11 kHz. Also, one of the amplifier poles is transferred to 43 kHz while the other two are much higher in frequency. Thus, the closed-loop system acts almost like a first-order system with a bandwidth of about 11 kHz (set by the light pole) and no stability problems. This example also shows that because the light-dependent pole acts as a dominant pole for the system, there are no potential stability problems due to the existence of three amplifier poles.

Suppose that the desired 8000 gain is implemented with a single amplifying stage. In this case, the feedback loop has 1 open-loop light pole at 1 Hz, a single open-loop amplifier pole at $2\times10^6/8000=250$ Hz, and a loop gain of 8000. Note that the amplifier pole is now 400 times slower than the amplifier poles above at the same overall gain, meaning that the effective GBW of the amplifier is much smaller. When the feedback loop is closed, a root locus plot illustrates that these two poles come together and depart from the real axis and form a complex pair at a frequency of 1.4 kHz and with a Q of 5.6. Therefore, not only does the single-stage-amplifier system have a final bandwidth that is almost eight times smaller than the three-stage system, it exhibits poor transient response and large overshoot, which makes it practically unusable. This example demonstrates the merits of distributing the gain over many stages in the photoreceptor design of the present invention.

Figure 5B:
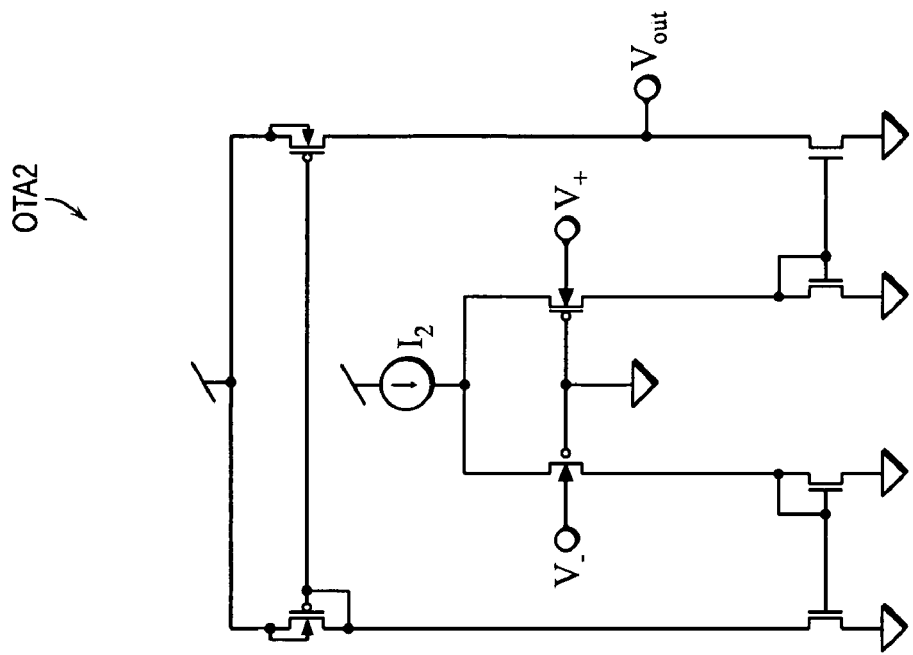
FIG. 5b is a circuit implementation of OTA2 blocks utilized in the distributed amplifier of FIG. 4.
Figure 5A:
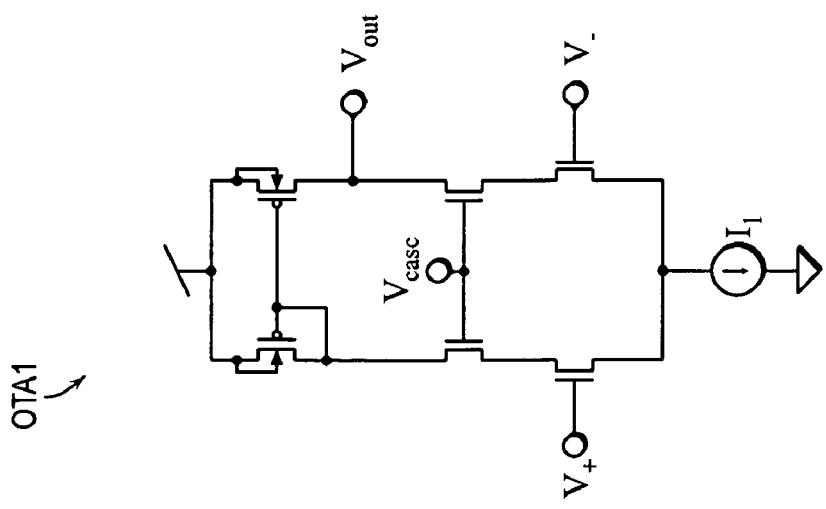
FIG. 5a is a circuit implementation of OTA1 blocks utilized in the distributed amplifier of FIG. 4 of the present invention.

As shown in the energy-efficient photoreceptor apparatus 40 of FIG. 4, six operational transconductance amplifier blocks (three OTA1 blocks of FIG. 5a and three OTA2 blocks of FIG. 5b) form an exemplary three-stage distributed amplifier 41. These blocks have an input-output relationship defined by: $i_{out}=G_{mi}(v_{in+}-V_{in-})_{i=1,2}$ where $G_{mi}$ is proportional to $I_i$. This relationship implies that the OTA2 blocks of FIG. 5b, in which the output terminal is connected to the negative input terminal, act like resistors of value $1/G_{m2}$. Thus, the total gain of the three-stage distributed amplifier 41 is $(-G_{m1}/G_{m2})^3$. The circuit implementations of the specific OTA1 and OTA2 blocks utilized in the photoreceptors of the present invention are displayed in FIGS. 5a and 5b. In FIG. 5a, OTA1 is a cascode differential amplifier 41 with active load. In FIG. 5b, OTA2 is a wide output-voltage range differential amplifier that uses the well (body) terminals of the two input PMOS transistors, instead of their gates, to lower the transconductance of the block (i.e. $G_{m2}$) and increase the overall gain of the distributed amplifier 41 of the present invention.

Another improvement in the photoreceptor apparatus 40 of FIG. 4 is to incorporate an adaptive loop gain control circuitry 42 to automatically adjust its loop gain based on the light intensity of the photocurrent signal 19. With an increase in light, $V_f$, $V_{cnt}$, $I_2$ and finally $G_{m2}$ rise and the gain of the distributed amplifier 41 drops (and vice versa). The photoreceptor apparatus 40 then exhibits less speedup for high light levels (to prevent potential instability due to interactions of light pole and 3 amplifier poles) and more speedup for low light levels (to achieve the target bandwidth required in the pulse oximeter system 10 of the present invention).

The voltage $V_f$ is averaged by the LPF block in FIG. 4, such that the gain control mechanism only responds to changes in the average light intensity. Blocks marked "x⅓" and "Level Shifter" in FIG. 4 adjust the gain and the offset of the control variable $V_{cnt}$. The one-third factor arises from the fact that there are three gain stages and the product of the gains of the three stages $-(G_{m1}/G_{m2})^3$ is selected to be approximately invariant with intensity. This is equivalent to requiring that the change in $G_{m2}$ with intensity follow a one-third power law. The apparatus 40 of FIG. 4 implements this condition since $V_f$ changes logarithmically with intensity and the $G_{m2}$ of OTA2 changes exponentially with its gate voltage in subthreshold operation. A more exact analysis shows that this power needs to be $1/(3K)$ if all the $G_{m2}$ amplifiers operate in subthreshold and $2/(3K)$ if all the $G_{m2}$ amplifiers operate above threshold. Experimentally, this photoreceptor apparatus 40 was able to achieve a closed-loop bandwidth that was nearly invariant over three orders of magnitude of light intensity.

In a configuration similar to that of each gain stage of the distributed amplifier, the $G_m$ ratio of two OTAs implements the scaling factor "x⅓" in the adaptive loop gain circuitry of FIG. 4. However, the transfer curves of these OTAs features an exponential sinh I-V characteristic that is implemented by using a sinh resistance, sinhR. The sinh resistance quickens the response time of the adaptive loop gain control circuitry 42 to large input transients, and thus improves its stability.

Another improvement is unilateralization, or the use of a common-gate stage (i.e. transistor $Q_4$) in the photoreceptor apparatus 40 of FIG. 4 to sense the input photocurrent 19 and convert it to a logarithmic voltage output signal. This transistor $Q_4$ removes the unwanted feed-through coupling due to the gate-to-source capacitance $C_{par}$ in FIG. 3, which limits the speedup and bandwidth of the photoreceptor's 40 transimpedance feedback loop by creating an unwanted zero in it. The gate-to-source capacitance of $Q_4$ is shorted to an AC ground at $V_{b4}$ in FIG. 4 and does not cause feed-through. Note that a source-follower stage (i.e., transistor $Q_1$) is still needed to ensure that no DC current flows through $R_1$. However, the feed-through coupling caused by the gate-to-source capacitance of this source follower is at a very high frequency because 13 is a relatively large bias current rather than a small light-dependent current such that there are no bandwidth-limiting effects in the loop.

B. Probe

In the pulse oximeter 10 of the present invention, a finger clip transmittance reusable probe 15 may be used as the sensing element, for e.g. the model 8000AA probe manufactured by Nonin Medical, Inc., Plymouth, Minn. As discussed above, the probe 15 of FIG. 1 consists of two small and high-intensity red and IR LEDs 12, 14, respectively, and a silicon photodiode 16 placed on the opposite side of the LEDs 12, 14. Each of these components is housed in an optically-shielded package that is coated with black material in its interior and an opaque plastic cover to prevent unwanted reflection and optical interference. To minimize the number of wires in the probe 15 (and hence the weight and cost), the LEDs 12, 14 are wired in a parallel arrangement with polarities reversed. The probe may be further adapted and configured in conjunction with a display unit (not shown) for displaying a level of the output signal to a user.

C. Oscillator/LED & Switching Control

Figure 6:
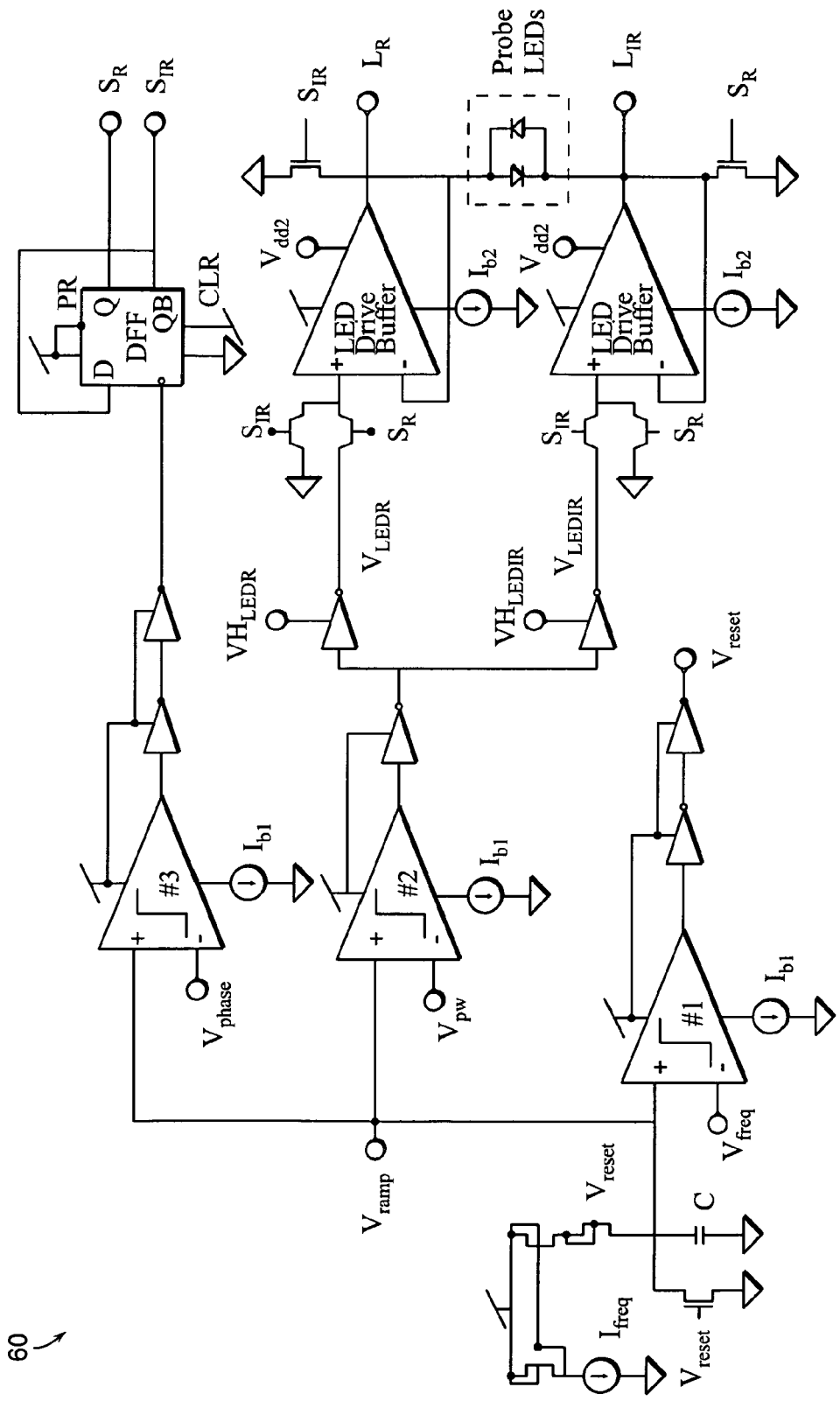
FIG. 6 is a circuit implementation of the oscillator/LED & switching control block of FIG. 1 according to the present invention.

The circuit implementation of the oscillator/LED & switching control block 60, shown in FIG. 6, is responsible for generating and synchronizing the required LED drive and current switching pulses in FIG. 1. The core of this oscillator/LED & switching control block 60 is a relaxation oscillator, which takes advantage of the periodic charging/discharging of a capacitor to generate an oscillation at adjustable switching frequency $f_s$. This core, shown in the bottom left corner of FIG. 6, consists of a current source ($I_{freq}$), a capacitor (C), a comparator (#1), and switches to reset the voltage of the capacitor. The generated oscillating ramp signal is used by other comparators, DFF, and switches to produce and synchronize the LED drive ($L_R/L_{IR}$) and current switching ($S_R/S_{IR}$) pulses.

The oscillator/LED & switching control block 60 also supplies the mA current levels required to illuminate LEDs 12, 14 by the employment of two LED drive buffers which are essentially voltage buffers designed to provide large amount of currents to their output load. The circuit structure of each buffer is composed of a conventional differential pair amplifier followed by a class AB output stage. The oscillator/LED & switching control block 60 is designed to be fully programmable. Specifically, the user can adjust the pulse frequency, the LED pulse amplitude, the LED pulse width (or duty cycle), and the relative phase between the LED and switching pulses by controlling $I_{freq}$, $VH_{LEDR}/VH_{LEDIR}$, $V_{pw}$, and $V_{phase}$, respectively.

D. Low-Pass Filters

Figure 7:
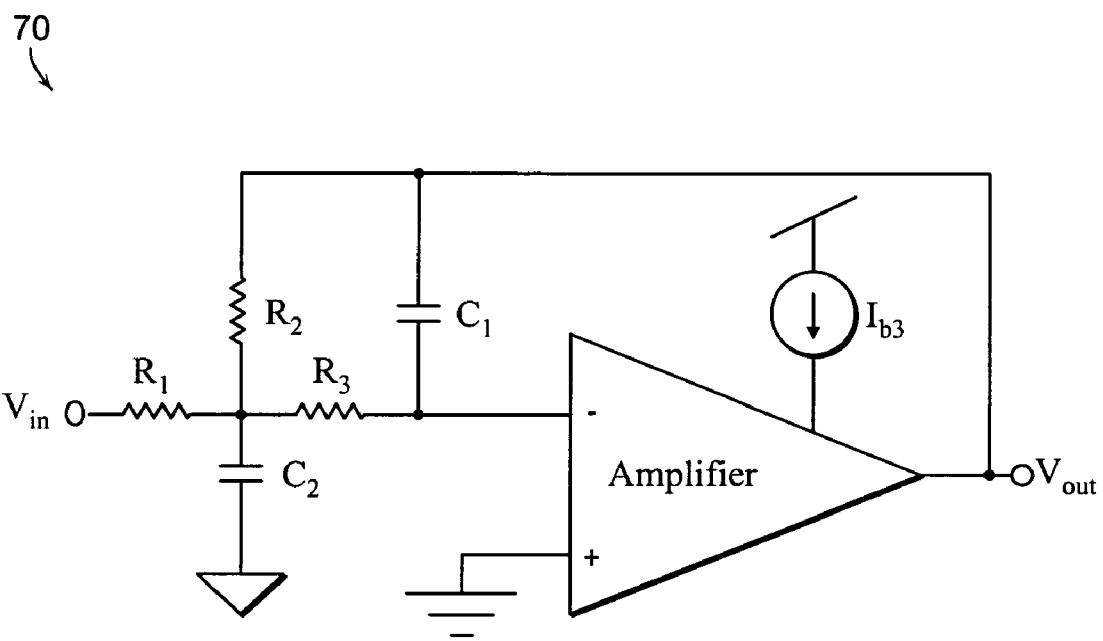
FIG. 7 shows the topology of a known active second-order low-pass filter.

Low pass filters (LPFs) 70 of FIG. 7 are placed after logarithmic transimpedance amplifiers 22, 24 in the pulse oximeter system 10 of FIG. 1 to attenuate switching frequency components and extract blood pulsation signals. Each of the filters in FIG. 1 has a forth-order roll-off achieved by cascading two standard active second-order Butterworth LPFs 70 with the topology displayed in FIG. 7. It is straightforward to find the transfer function of this circuit to be $$H(s) = \frac{V_{out}}{V_{in}} \quad (5)$$
$$= \frac{-1}{s^2 R_1 R_3 C_1 C_2 + sC_1\left(R_1 + R_3 + \frac{R_1 R_3}{R_2}\right) + \frac{R_1}{R_2}}$$
$$= \frac{A_v}{\tau^2 s^2 + \frac{\tau}{Q}s + 1}$$

The design of the present invention is commensurate with the operating range of commercial pulse oximeters that are capable of handling a wide range of pulse rates, i.e., between 18-300 bpm or equivalently 0.3-5 Hz in frequency. These specifications imply that the corner frequency of the LPFs 70 need to be low enough to remove switching components (at $f_s$=100 Hz in the setup) as far as possible, but not so low as to prevent the attenuation of the signals in the pass-band of interest (which extends up to 5 Hz). Hence, the design of the LPF 70 of the present invention has an approximate frequency of 7 Hz and values for resistors and capacitors in FIG. 7 can be chosen accordingly. As the active element of the filter, a classic two-stage operational amplifier (a differential amplifier followed by a common-source stage) with a class AB output stage is utilized.

E. Ratio Computation

Figure 8:
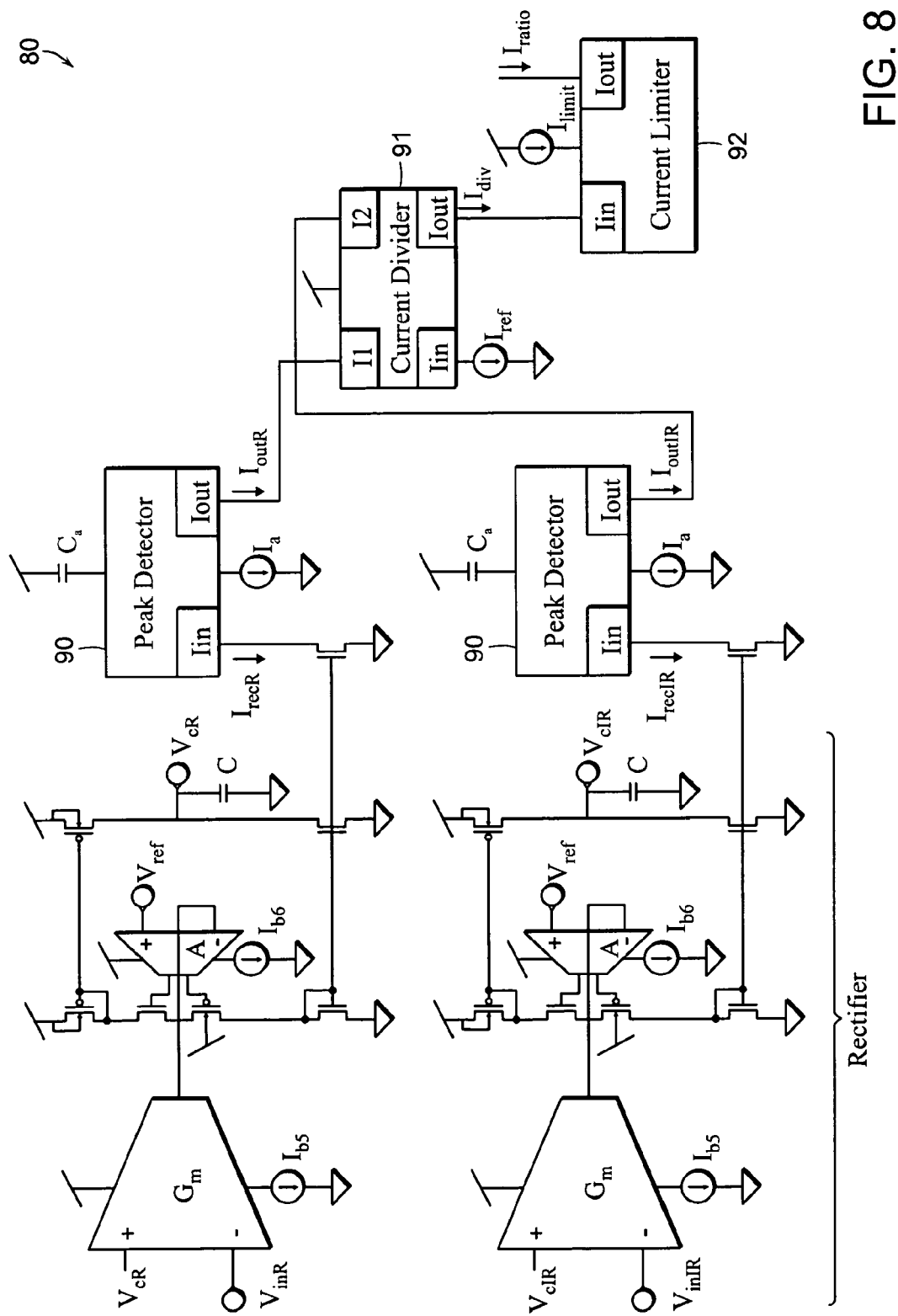
FIG. 8 shows the structure of the ratio computation block of FIG. 1.

FIG. 8 illustrates the structure of the ratio computation block 80 employed at the last stage of the pulse oximeter 10 of FIG. 1 to compute R. This block first detects the amplitudes of the red and IR blood pulsation signals (extracted by LPFs 70) through two modified current-mode envelope detectors and then computes their ratio by the use of a translinear current divider 91 to find R (refer to (2)).

The circuit implementation of each envelope detector is composed of a half-wave voltage-to-current-converting rectifier followed by a peak detector 90. The V-I conversion is performed through a transconductance amplifier ($G_m$ in FIG. 8). The current through the capacitor C is split into a positive half and a negative half by an intervening class-B mirror and only the negative half is mirrored to the input of the peak detector 90. The capacitor's current is a high-pass filtered version of the input voltage with its pole at $G_m/2\pi C$ (set to be 0.1 Hz in the design of the present invention). Thus, the response of the rectifier is not sensitive to input DC voltage and the offsets of the preceding blocks do not matter. The rectifier also features active feedback and dead-zone reduction schemes achieved by the use of a feedback amplifier (A) in FIG. 8.

Figure 9:
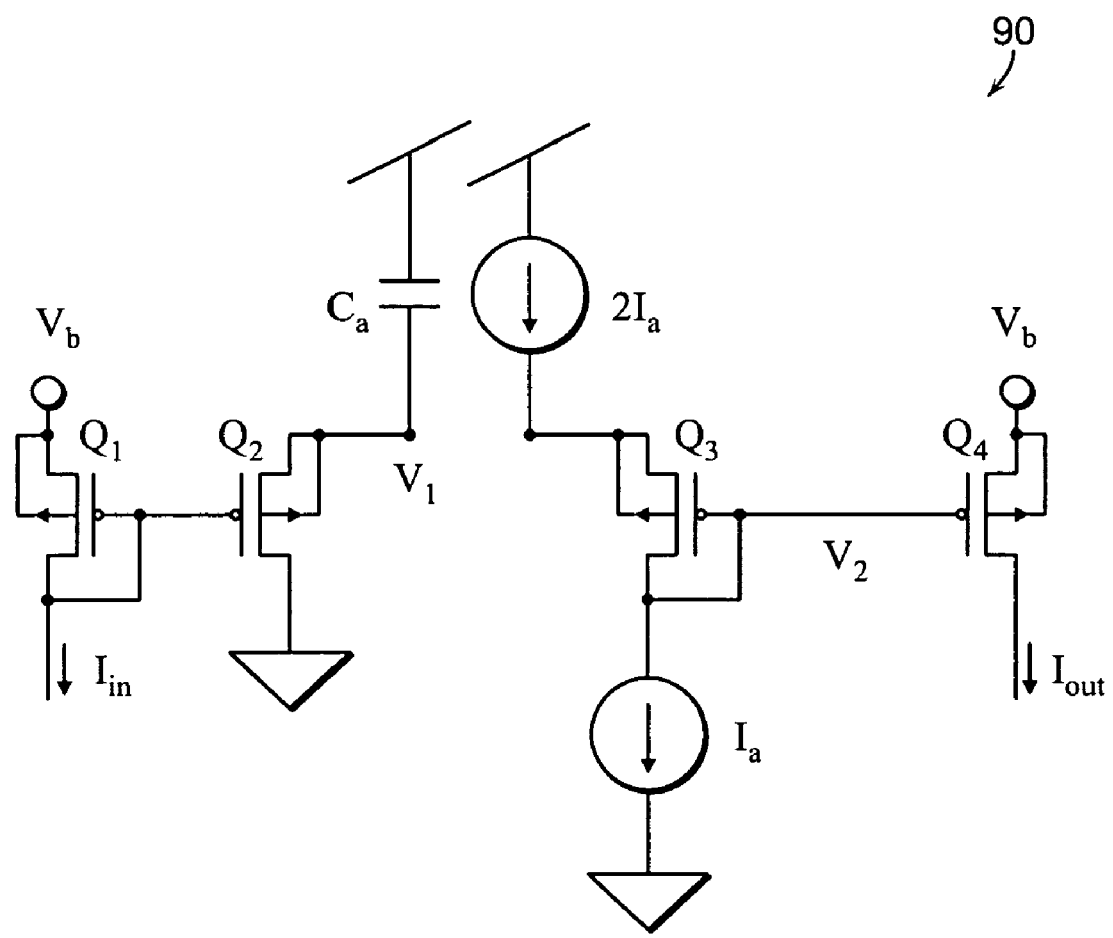
FIG. 9 is a circuit schematic for each of the peak detectors of FIG. 8.

The circuit schematic for each of the peak detectors 90 used in FIG. 8 is shown in FIG. 9. This circuit is essentially a current-mode first-order LPF topology that estimates the average of the rectified signal as a representative of its energy and exploits the translinear principle in its design. The pole frequency of the circuit in FIG. 9 is at $\kappa_p I_d/2\pi C_a U_T$ and can be designed to be 0.15 Bz in one embodiment of the present invention.

Figure 10A:
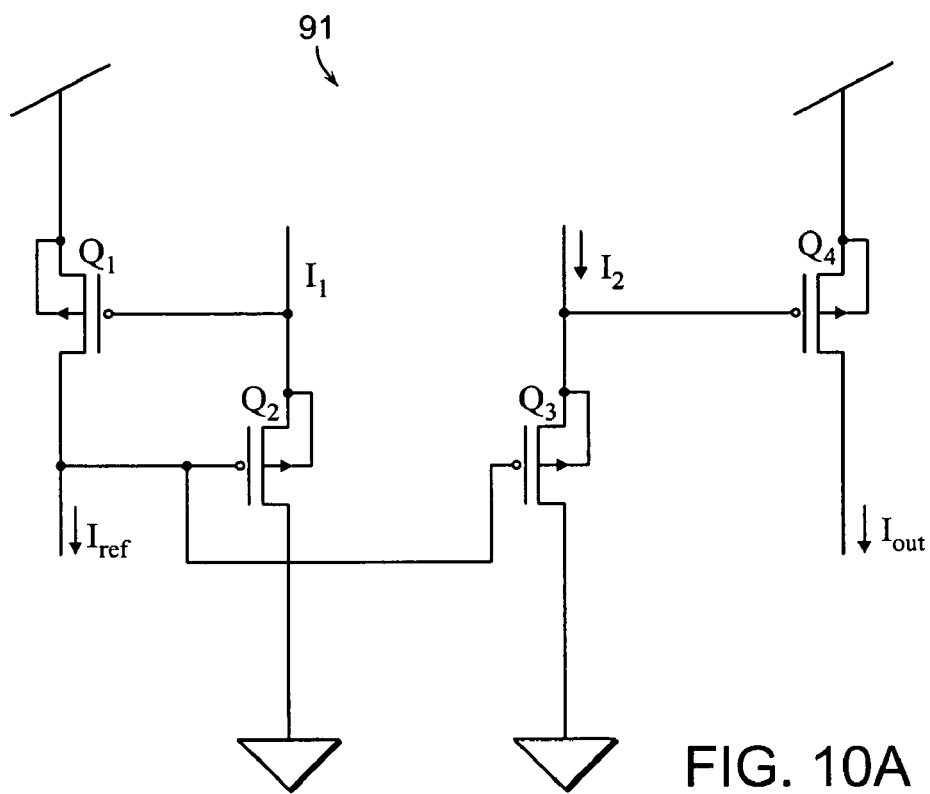
FIG. 10a is a circuit schematic of the current divider of FIG. 8.

FIG. 10a shows the circuit schematic of the current divider 91 circuit employed in the structure of FIG. 8. By applying the current-mode translinear principle, the input-output relationship of this circuit to be $I_{out}=I_{ref}(I_1/I_2)$ can be found.

Figure 10B:
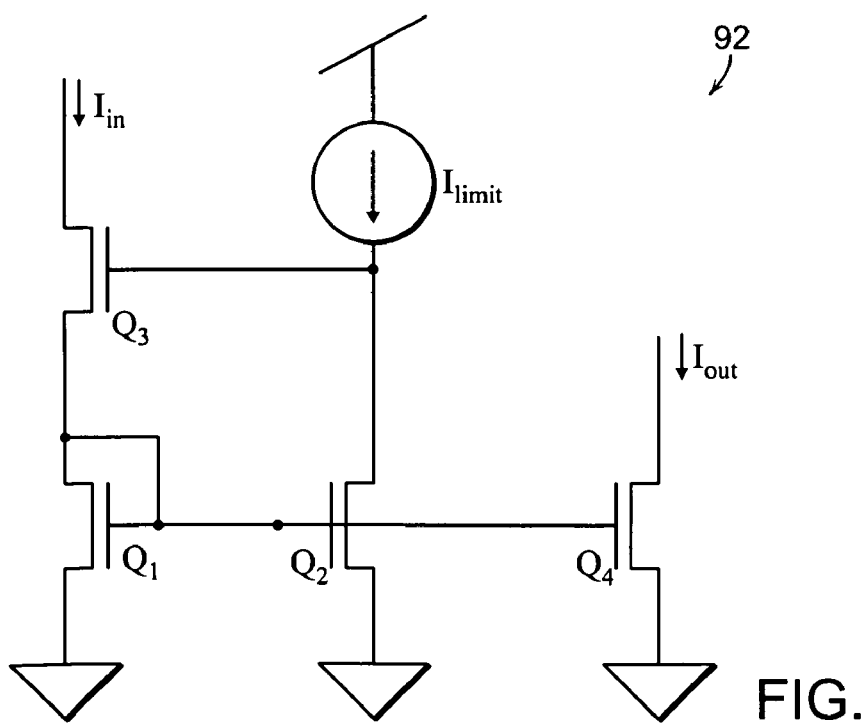
FIG. 10b is a circuit schematic of the current limiter of FIG. 8.

A problem that always arises in division or ratio circuits is that of dividing by zero when there is no input. When no tissue is present inside the oximeter's probe and thus no blood pulsation signals are detected, the output currents of the peak detectors 90 in FIG. 8 ($I_{outR}$ and $I_{outIR}$) are nearly zero. Consequently, a 0/0 division in the current divider 91 causes its output to become very large. This scenario significantly hurts the power consumption of the pulse oximeter system 10 when it is in standby mode. The solution is to employ a current-limiter block 92 as the last section of the ratio computation block 80 as shown in FIG. 8. This current limiter 92 imposes a ceiling on the magnitude of the output current. In other words, it sets its output ($I_{ratio}$) to be the minimum of its input ($I_{div}$) and an adjustable limit ($I_{limit}$) and therefore, discards uncharacteristically large values of R. The circuit implementation of the current limiter 92 is illustrated in FIG. 10b. This current limiter 92 adapts a standard Wilson current mirror configuration to have two inputs; negative feedback automatically drives the transistors that supply $I_{in}$ (=$I_{div}$) or $I_{limit}$ out of saturation and reduces their currents to that of the smaller input. The current output of the circuit is always the smaller of its two inputs.

Finally, when the pulse oximeter system 10 is measuring blood's oxygen saturation of a test subject, $I_{ratio}$ (which constitutes the output of the whole pulse oximeter system shown in FIG. 1) is equal to $$I_{ratio} = I_{div} \quad (6)$$
$$= I_{ref} \times \frac{I_{outR}}{I_{outIR}}$$
$$= I_{ref} \times \frac{v_{inR}}{v_{inIR}} \stackrel{(4)}{=} I_{ref} \times \frac{i_{ac\cdot R}/I_{DC\cdot R}}{i_{ac\cdot IR}/I_{DC\cdot IR}} \stackrel{(2)}{=} I_{ref} \times R$$

Thus, as mentioned before, the output of the pulse oximeter chip 11 is directly proportional to R. If a digital output is desired, then a digital representation of R may be obtained by computing $I_{ratio}/I_{ref}$ with an eight-bit version of an energy-efficient current-mode analog-to-digital converter consuming a few microwatts of power.

F. Reference Generator/Bias Circuitry

To attain temperature immunity and minimize the effects of power supply noise, almost all the necessary bias currents and voltages needed by different circuits throughout the pulse oximeter system are created on-chip 11 by a reference and then properly distributed to the low power circuits of the present invention through current mirroring and buffering. The core of this block is a thermal-voltage-referenced self-biased current source with appropriate start-up circuitry, reference generator/bias circuitry 9 shown connected to the oscillator/LED & switching control 60 by a dashed line in FIG. 1. Although this reference has very good immunity to power-supply noise, cascode mirroring and capacitive bypassing are implemented to further reduce the small remaining power-supply effects on the reference output.

III. Experimental Results

Figure 11:
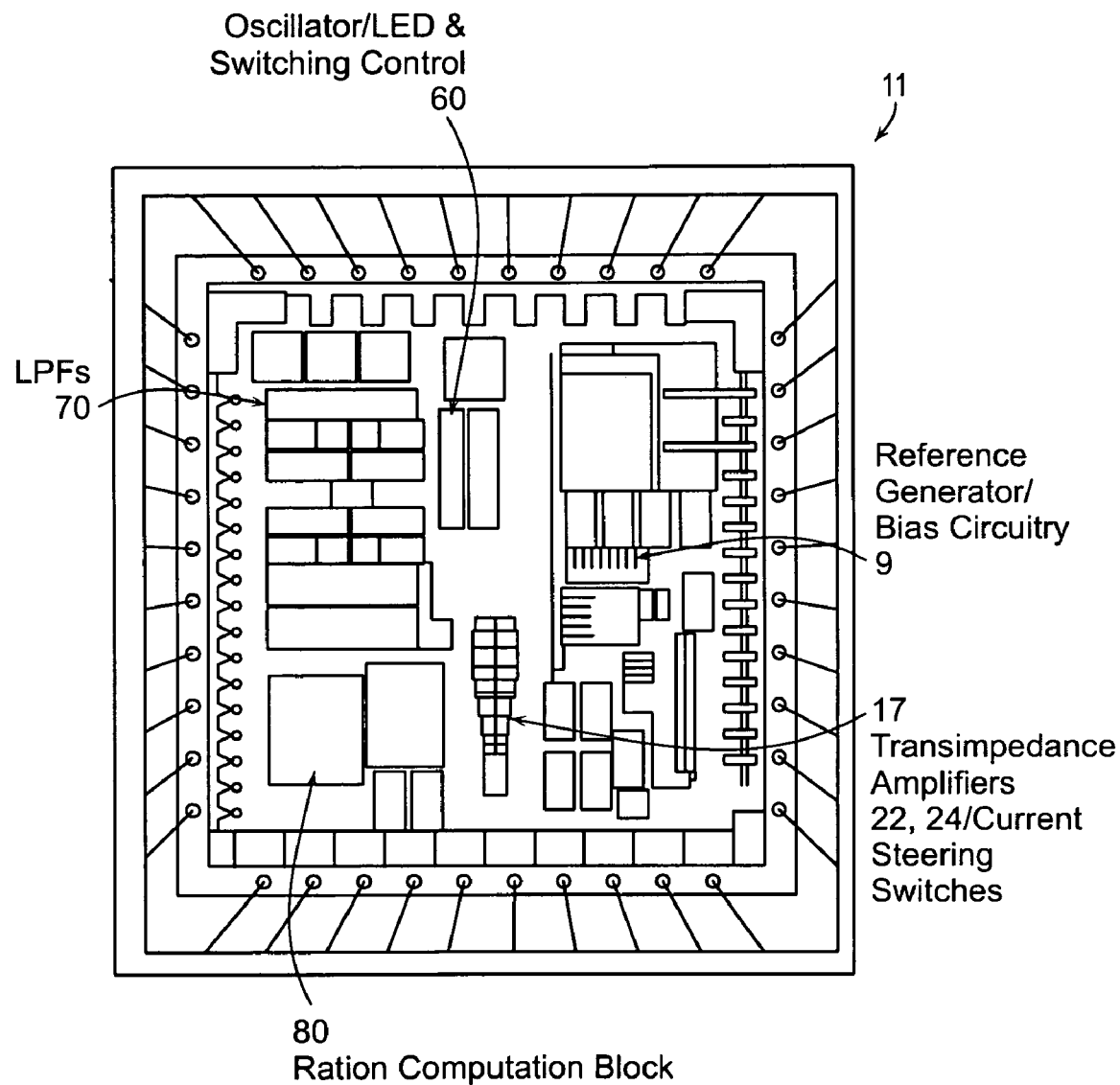
FIG. 11 is a photograph of a pulse oximeter chip implementation of FIG. 1.

FIG. 11 shows a die photograph of a chip 11, according to the present invention, containing the entire low-power pulse oximeter system 10 shown in FIG. 1. The chip 11 was fabricated in a 1.5 μm AMI BiCMOS n-well process available through MOSIS. All the pulse oximeter system 10 building blocks are also marked in FIG. 11. These blocks were individually fabricated on previous chips, tested, and debugged before all being fit into the complete pulse oximeter chip 11 of FIG. 11, which is 2.2 mm×2.2 mm in size.

Figure 12:
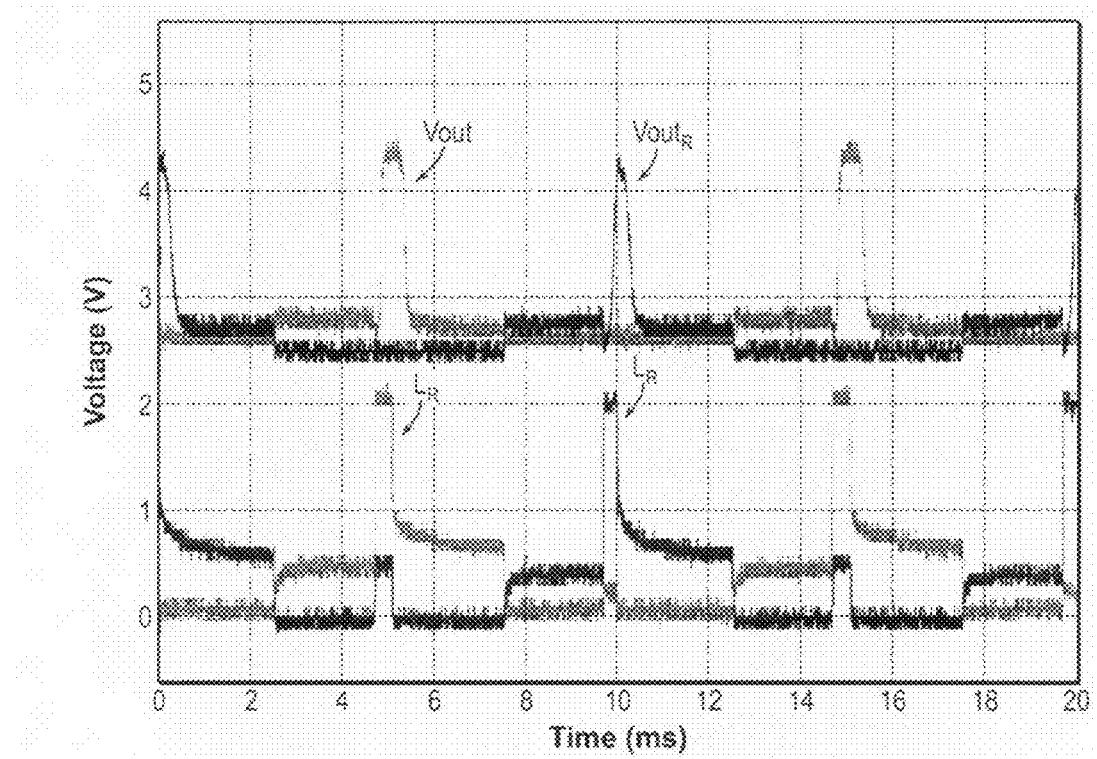
FIG. 12 is a voltage waveform measured at the output of the two logarithmic transimpedance amplifiers of FIG. 1.

The experimental output-voltage waveforms that typically appear at the output of the logarithmic photoreceptors 22, 24 (i.e. $Vout_R$ and $Vout_{IR}$ in FIG. 1) are shown in FIG. 12. These waveforms are measured in the case when a finger has been placed in the oximeter probe 15. The LED pulses ($L_R$ and $L_{IR}$), running at a frequency $f_s$ of 100 Hz each with a duty cycle of approximately 3%, are displayed in this FIG. 12 as well. It is observed that $Vout_R$ and $Vout_{IR}$ are composed of pulses that are responsive to the light pulses generated by red and IR LEDs 12, 14, respectively. This verifies that each photoreceptor responds only to its designated input light signal and hence the photocurrent 19 splitting is successfully performed by the current steering block.

Figures 13A, 13B:
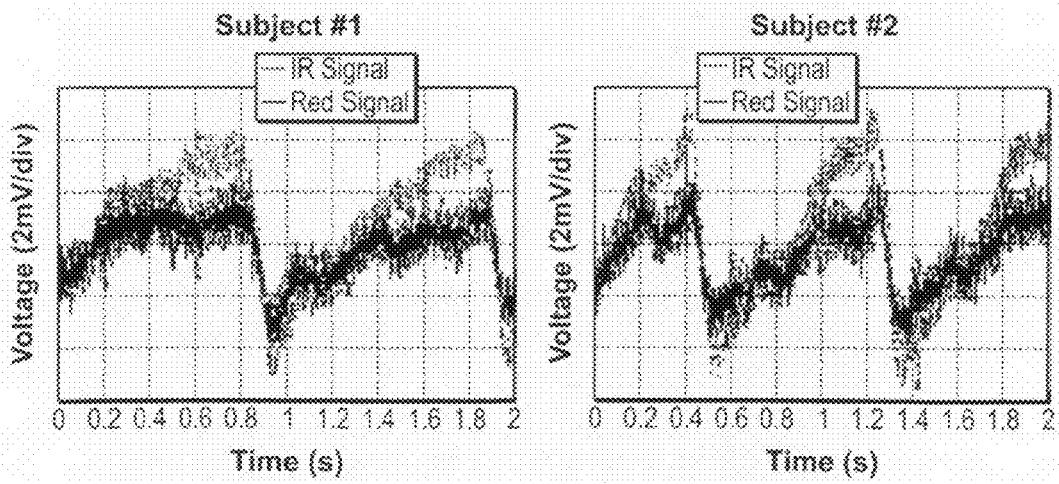
FIG. 13a shows a graph of measured blood pulsation signals of test subject #1 that appear at the outputs of the two LPFs in FIG. 1.
FIG. 13b shows a graph of measured blood pulsation signals of test subject #2 that appear at the outputs of the two LPFs in FIG. 1.
Figure 13C:
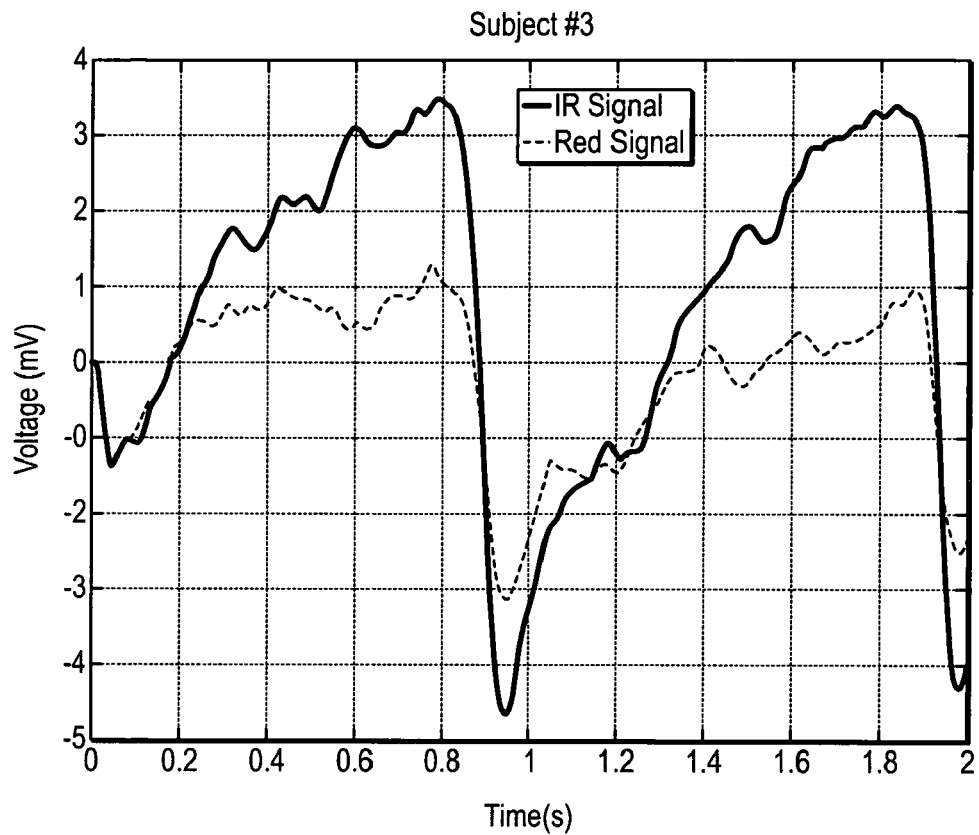
FIG. 13c shows a graph of measured blood pulsation signals of test subject #3 that appear at the outputs of the two LPFs in FIG. 1.

FIG. 12 shows that the amplitudes of the fast pulses of $Vout_R$ and $Vout_{IR}$ are slowly vibrating with a frequency equal to the heart rate of the subject under test ($f_p$). In other words, blood pulsations have AM modulated the voltage pulses at the output of the transimpedance amplifiers, as predicted. These blood pulsation signals, also known as plethysmographic or photoplethysmographic signals, are extracted by the LPFs 70 that follow the transimpedance amplifiers 22, 24 and appear at the output of these filters 70, as displayed in FIGS. 13a, 13b and 13c. FIGS. 13a-c show the graph of measured red and IR blood pulsation signals of three different subjects obtained by the pulse oximeter system 10. Although the absolute amplitudes of these signals are rather low (a few mV), the system 10 of the present invention is sensitive enough to detect them because its precision is only limited by the shot noise of the incoming light.

The plethysmographic signals of FIGS. 13a-c provide valuable information about the physiological conditions of the subjects under test, for example, the difference in the heart rates of subject #1, subject #2 and subject #3. More importantly, the ratio of the red over infrared signal of each subject determines R, which is directly related to her blood-oxygen saturation ($S_pO_2$). The waveform of subject #3 in FIG. 13c shows less oscilloscope and other instrumentation noise since these artifacts were removed through digital filtering after the data were acquired.

As discussed above, the pulse oximeter 10 of the present invention requires calibration to relate R to $S_pO_2$. To perform such calibration, relatively cheap devices are available in the market that simulates the optical properties of the human finger. Here, three commercially available translucent artificial fingers are used, built with colored materials to simulate arterial blood at 80%, 90%, and 97% oxygen saturation levels, respectively.

Figure 14:
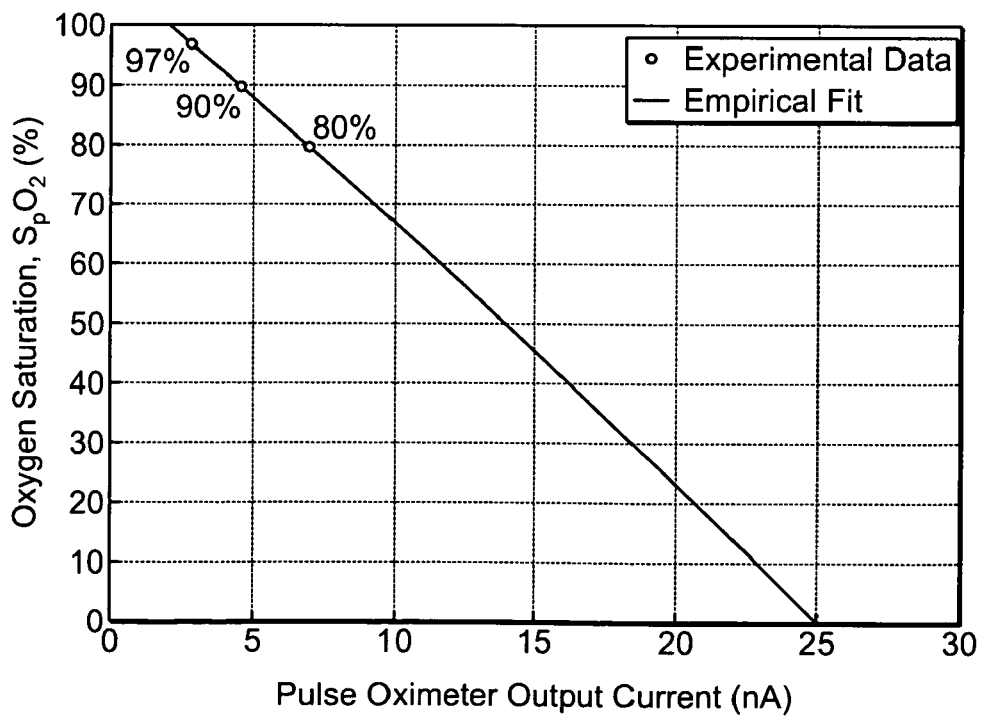
FIG. 14 shows the second-order empirical calibration curve relating the output current of the pulse oximeter to the blood-oxygen saturation of a test subject according to the present invention.

To calibrate the pulse oximeter system 10 of the present invention, each of the calibration fingers inside the probe 15 are manually pressed and the output current of the oximeter 10 is measured. With these three available data points (each of which is an average value of 180 current readings), an exact second-order polynomial curve can be plotted, which is the relationship utilized in most commercial pulse oximeters. The calibration curve is plotted in FIG. 14 and is important because it relates the output current of the oximeter chip 10 $I_{ratio}$ (adjusted to be $I_{ref} \times R = 5nA \times R$) to the oxygen saturation of the subject under test. Mathematically, this relationship can be expressed as $$S_pO_2 = 108 - 4.0 \times 10^9 I_{ratio} - 1.5 \times 10^{16} I_{ratio}^2 = 108 - 20R - 0.375R^2 \quad (7)$$

After the pulse oximeter 10 is calibrated, the blood-oxygen saturation of real subjects is measured and compared the readings with a reference. A commercial Nonin® digital handheld pulse oximeter, model PalmSAT® 2500, is used as a reference. Table I lists the oxygen saturation ($S_pO_2$) of various individuals measured by the pulse oximeter 10 of the present invention and a reference pulse oximeter at the same time. The output current readings of the pulse oximeter 10 of the present invention associated with each subject are also reported in this table. By statistically analyzing the differences between the oxygen readings of the pulse oximeter 10 and the reference oximeter, it is shown that the pulse oximeter 10 of the present invention differs from the Nonin® readings by a mean of −1.2% and the standard deviation of differences is 1.5%. Since the accuracy of most pulse oximeters is approximately 2% and the medical use of pulse oximetry does not require precision beyond this level, the pulse oximeter system 10 of the present invention is a commercially viable solution.

TABLE I

BLOOD-OXYGEN SATURATION OF VARIOUS SUBJECTS MEASURED BY THE PULSE OXIMETER OF THE PRESENT INVENTION IN COMPARISON TO A REFERENCE PULSE OXIMETER

| Subject | Pulse Oximeter Output Current ($I_{ratio}$) Readings of the present invention | Pulse Oximeter Oxygen Saturation ($S_pO_2$) Readings of the present invention | Reference Pulse Oximeter Oxygen Saturation ($S_pO_2$) Readings |
|---|---|---|---|
| #1 | 3.2 nA | 95% | 98% |
| #2 | 3.1 nA | 95% | 97% |
| #3 | 3.6 nA | 93% | 95% |
| #4 | 3.3 nA | 95% | 95% |
| #5 | 2.9 nA | 96% | 95% |
| #6 | 3.2 nA | 95% | 97% |
| #7 | 3.0 nA | 96% | 95% |
| #8 | 2.9 nA | 96% | 98% |
| #9 | 2.8 nA | 96% | 99% |
| #10 | 3.1 nA | 95% | 95% |
| #11 | 2.8 nA | 97% | 98% |

A primary objective in designing a new pulse oximeter system 10 is the reduction of power consumption as far as possible without sacrificing any critical medical properties of the device. Therefore, the power requirement is carefully examined during various stages of operation of the pulse oximeter 10 according to the present invention. The measured power dissipation of each of the building blocks of the pulse oximeter system 10 is listed in Table II. It can be observed that the total power consumption of the pulse oximeter 10 adds up to 4.8 mW. The power dissipation of the oscillator/LED & switching control block 60, which is mostly spent to drive and illuminate the two red and IR LEDs 12, 14, dominates the power requirement of the whole pulse oximeter system 10. In fact, the total power dissipation of all the other parts of the system, which constitute the oximeter's processing unit, does not exceed 400 μW or 8.5% of the total power. Further, power dissipation in the range of 1 μW to 400 μW can be obtained in accordance with the present invention.

TABLE II

MEASURED POWER DISSIPATION FOR EACH OF THE INDIVIDUAL BLOCKS OF THE PULSE OXIMETER SYSTEM SHOWN IN FIG. 1.

| Power Consumption per Block | Value | |
|---|---|---|
| Oscillator/LED & Switching Control | 4.4 mW | |
| Two Transimpedance Amplifiers | 80 μW | |
| Two Low-pass Filters | 300 μW | Less than |
| Ratio Computation | 2.2 μW | 400 μW of |
| Reference Generator/Bias Circuitry | 11.5 μW | processing power |
| Total | 4.8 mW | |

Finally, Table III compares the total power dissipation of pulse oximeter system 10 with several low-power commercial pulse oximeters. Using a multimeter, the current that is drawn from the batteries of these oximeters is directly measured with the display inactive and active. The numbers reported in Table III do not include display power consumption, just LED and processing power consumption. It can be observed that the pulse oximeter system 10 consumes about 11 times less power than the best commercial pulse oximeter (Nonin® model WristOx® 3100). The tangible consequence of such power savings is that, while the batteries in the WristOx® 3100 oximeter need replacement/recharging every 5 days, the same batteries can power up the pulse oximeter 10 of the present invention for 2 months.

TABLE III

A COMPARISON OF THE POWER CONSUMPTION OF THE PULSE OXIMETER OF THE PRESENT INVENTION WITH A NUMBER OF COMMERCIALLY AVAILABLE PULSE OXIMETERS

| Pulse Oximeter Version | Total Power Consumption (LED power and processing power, excluding display) | Days in Operation on 4 "AAA" Batteries |
|---|---|---|
| Present Invention | 4.8 mW | 60 |
| WristOx ® 3100 | ~55 mW | 5.2 |
| Xpod | 60 mW | 4.8 |
| Ipod | 60 mW | 4.8 |
| Avant ® 4000 | 71 mW | 4 |
| PalmSAT ® 2500 | ~80 mW | 3.6 |
| Onyx ® 9500 | ~120 mW | 2.4 |
| 8500 Series | ~130 mW | 2.2 |

Figure 15:
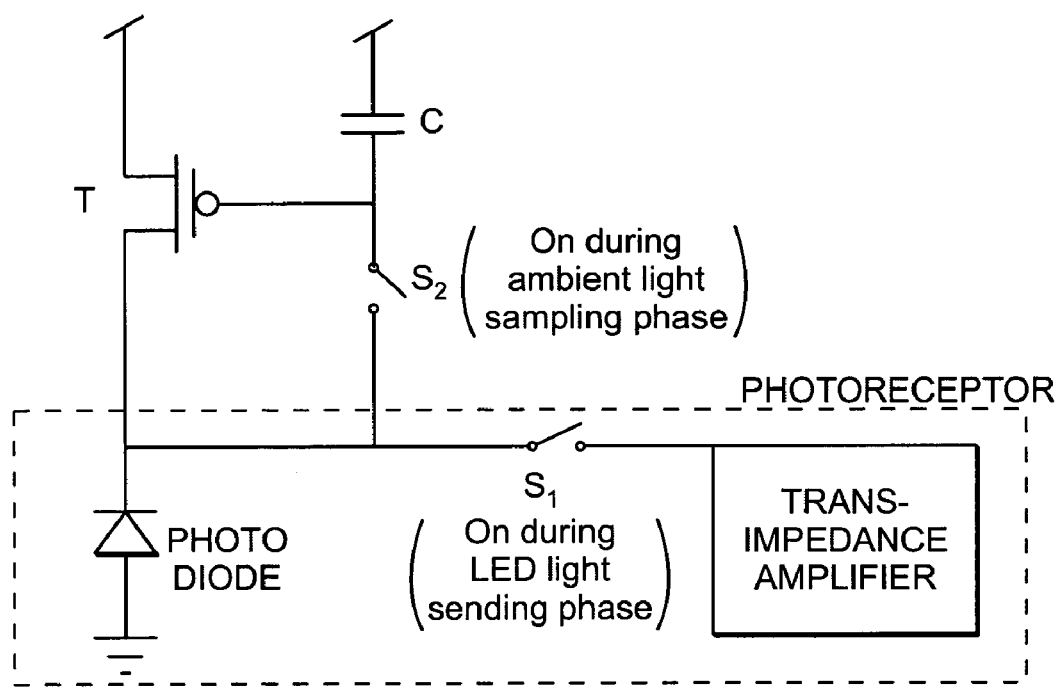
FIG. 15 is a circuit schematic of an ambient light subtractor used in the present invention.

Although the fabricated pulse oximeter chip 11 of the present invention currently dissipates considerably less power than other existing oximeters, it has been shown above that it is potentially possible to reduce the power consumption even further to around 1 mW with a better fabrication technology (a 1.5 μm technology is used), higher power supply, and more area consumption. Beyond this optimal point, the photoreceptor apparatus of the present invention would have to burn more power than the LEDs 12, 14 to sense their reduced input light intensity such that the total power requirement of the pulse oximeter 10 would rise again. Therefore, the pulse oximeter system 10 design could be potentially utilized to construct pulse oximeters that require 55 times less operational power than the best commercial pulse oximeters of today. Simple extensions to the adaptive energy-efficient photoreceptor disclosed herein can be combined with other well known techniques to further improve performance, e.g. subtraction of ambient light during a sampling phase as shown in FIG. 15, the use of the photoreceptor in multi-wavelength pulse oximeters, signal processing with digitized outputs of the transimpedance amplifier to remove motion artifacts and circuitry for adapting the LED power to the subject.

The energy-efficient low-power pulse oximeter 10 achieves more than an order-of-magnitude reduction in power consumption over the best commercial pulse oximeters, and yields similar performance as confirmed with experimental measurements. Most of this reduction is due to the use of a photoreceptor that is inherently sensitive to the signals required for pulse oximetry computations, and which is built with distributed amplification, adaptive loop gain control, and unilateralization. Consequently, the dominant source of power consumption, LED power, can be significantly reduced. The pulse oximeter system 10 of the present invention is suited for use in emerging portable and wearable medical applications where battery life is of paramount concern.

Although the gain of the amplifier used in the energy-efficient photoreceptor apparatus 40 of FIG. 4 cannot be increased beyond its current (very large) value due to practical limitations, it is possible to determine how to reduce the total power consumption of the pulse oximeter system 10 without this gain constraint.

It can be further shown that the closed-loop bandwidth (BW) of the transimpedance amplifier 24 shown in FIGS. 1 and 4 in terms of the photocurrent 19 ($I_1$) and amplifier's gain ($A_{amp}$) is calculated by $$BW = \frac{1}{2\pi T_{in}} \times (1 + A_{ip}) \approx \frac{I_1}{2\pi U_T C_{in}} \times A_{amp} \times \left(\frac{\kappa_1 C_1}{C_1 + C_2}\right) \quad (8)$$

BW has to always be larger than a certain limit so that the transimpedance photoreceptors 22, 24 and photodiode 16 completely turn ON and settle down in the short ON duration of LED pulses to ensure proper conversion, distribution, and processing of the input red and IR photocurrents 19 (e.g. BW=2.1 kHz). Also, note that $I_1$ is directly proportional to the drive current of LEDs 12, 14 or equivalently to the LED power ($P_{LED}$). Thus, for a fixed BW $$\frac{I_{1'}}{I_1} = \frac{P_{LED'}}{P_{LED}} \quad (9)$$

$$= \frac{A_{amp}}{A_{amp'}} \Rightarrow P_{LED'} - 4.4 \text{ mW} \times \frac{A_{amp}}{A_{amp'}}$$

$$= (4.4 \text{ mW}) x^{-1}$$

where $P_{LED}$=4.4 mW is the LED power at its current setting (see Table II above) and $x = A_{amp'}/A_{amp}$ is equal to the extra gain that the transimpedance amplifier 22, 24 needs at the optimum condition (that will be calculated below.) Note that "parameter'" and "parameter" represent the optimum and current values of a parameter, which is used in this analysis, respectively.

The power consumption of the transimpedance amplifiers 22, 24 ($P_{PR}$) must be expressed in terms of x as well. Assume that the majority of this power is burnt within transconductors OTA1 in the circuit of FIG. 4 to provide a large gain for the distributed amplifier and speedup the input light pole. Consequently, $$\frac{P_{PR'}}{P_{PR}} = \frac{I_{1'}}{I_1} \tag{10}$$

$$= \left(\frac{G_{m1'}}{G_{m1}}\right)^2$$

$$= \left(\frac{A_{amp'}}{A_{amp}}\right)^{2/3} \Rightarrow P_{PR'} = 80 \ \mu W \times \left(\frac{A_{amp'}}{A_{amp}}\right)^{2/3}$$

$$= (80 \ \mu W) x^{2/3}$$

where $P_{PR}=80$ μW is the current value for photoreceptors power (see Table II) and it is assumed that the transistors in OTA1 are operating above threshold because their bias current ($I_1$) is relatively large.

Ignoring the power dissipations of the two low-pass filters, the ratio computation block 80, and the reference generator/bias circuitry block 9, the overall approximate power requirement of the pulse oximeter system 11 of the present invention is determined by the LEDs 12, 14 and the transimpedance amplifiers 22, 24. Therefore, $$P_{TOT}'(x) = P_{LED}' + P_{PR}' = (4.4 \text{mW})x^{-1} + (80 \mu W)x^{2/3} \tag{11}$$

From this equation, it is expected that an optimum point in which the total power consumption of the pulse oximeter 10 ($P_{TOT}$) has a minimum. Analysis shows that this optimum happens at x=14.1, indicating that if the transimpedance amplifier's gain could be increased by a factor of 14.1, the total power dissipation could be reduced to $P_{TOT}'$=780 μW, a factor of 5.7 lower than its current value of $P_{TOT}$=4.48 mW. However, making the gain larger than this optimum would not help because the photoreceptor power would exceed the LED power and hurt the total power dissipation of the chip 11.

The 14.1 factor decrease in LED power could be accomplished by either reducing the LED drive currents by this factor or lowering the duty cycle of the chopped LED pulses. In any case, the average LED-generated photocurrent 19 would drop from its current 50 nA value (typically) to about 3.5 nA.

It is also important that ambient light and minimum detectable contrast of the sensor do not limit the performance of the pulse oximeter of the present invention because of the reduction in LED power. The photocurrent produced in the photodiode 16 due to ambient light in the present invention is approximately 3 nA, smaller than the LED-generated photocurrent 19. Well-known techniques to subtract the ambient light in a calibration phase may be used. FIG. 15 shows an example ambient light subtractor according to the present invention, wherein the subtraction takes place by means of two switches S1, S2, a capacitor C and a transistor T in a sampling and sensing phase as shown in FIG. 15.

The minimum detectable contrast of the transimpedance amplifier 22, 24 at this photocurrent level must also be calculated to make sure that it is still lower than 0.5%, the smallest contrast (AC/DC) of the blood-modulated input light that is typically encountered in pulse oximetry. It has been shown that it is less than 0.1%, even at such low light levels.

The total voltage noise contributed by all the building blocks in FIG. 1 shows that the oximeter's noise is dominated by the noise of its front-end transimpedance amplifiers, as it should be in any good design. Dividing this noise by the gain relationship of (4), the minimum detectable contrast is found to be $$\left(\frac{i_{ac,1}}{I_{DC,1}}\right)_{min} = \sqrt{\frac{2\pi q \times BW}{I_{DC,1}}} \tag{12}$$

where $I_{DC,1}$ is the average photocurrent 19 flowing into transimpedance amplifiers 22, 24. Even with $I_{DC,1}$=3.5 nA, the minimum detectable contrast is less than 0.1%.

It is important to note that the extra 14.1 increase in the gain of the distributed amplifier in FIG. 4 could be achieved by supplying 5.8 times more bias current $I_1$ to OTA1 transconductors of FIG. 5a. This strategy would cause a 2.4-fold rise in the voltage overdrive of the transistors in OTA1 or require the use of 5.8-times wider transistors to keep their voltage overdrive at the current level.

While the invention has been described with reference to specific embodiments, those skilled in the art will readily appreciate that the invention can be practiced with modifications within the spirit and scope of the appended claims, i.e. changes that can be made in form and detail, without departing from the spirit and scope of the invention. Accordingly, all such changes come within the purview of the present invention, and the invention encompasses the subject matter of the claims, which follow.

What is claimed is:

1. A transimpedance amplifier apparatus for providing energy-efficient amplification and feedback conversion of an input-current signal into an output-voltage signal comprising:
    a) a high-gain amplifier connected between an input and an output of the transimpedance amplifier apparatus wherein the high-gain amplifier is comprised of a cascade of at least three successive lower-gain amplification stages; and
    b) a feedback network connected between the output and input of the transimpedance amplifier apparatus that determines an overall gain from input to output of the transimpedance amplifier apparatus; and
    c) an adaptive-loop-gain means, for adjusting an amount of amplification provided by the high-gain amplifier based on one of the level of the input-current signal, the level of the output signal, and the gain of said feedback network.

2. The transimpedance amplifier apparatus of claim 1, wherein all of the lower-gain amplification stages have substantially identical gains to maximize the energy-efficiency of the transimpedance amplifier apparatus.

3. The transimpedance amplifier apparatus of claim 1, wherein the adaptive-loop-gain means adjusts the gain of at least one of the amplification stages such that the overall bandwidth of the transimpedance amplifier apparatus is nearly constant at all input levels.

4. The transimpedance amplifier apparatus of claim 1, wherein the adaptive-loop-gain means adjusts the gain of at least one of the amplification stages such that the overall bandwidth of the transimpedance amplifier apparatus is substantially constant at all gain settings of said feedback network.

5. The transimpedance amplifier apparatus of claim 1, wherein the adaptive-loop-gain means adjusts the gain of at least one of the amplification stages such that the overall bandwidth of the transimpedance amplifier apparatus is substantially constant and independent of an overall gain of the transimpedance amplifier apparatus.

6. The transimpedance amplifier apparatus of claim 1, wherein the adaptive-loop-gain means adjusts the gains of the amplification stages such that the feedback loop of the transimpedance amplifier apparatus is stable at all input-current levels.

7. The transimpedance amplifier apparatus of claim 1, wherein the adaptive-loop-gain means adjusts the gains of the amplification stages such that the feedback loop of the transimpedance amplifier apparatus is stable at all gain settings of said feedback network.

8. The transimpedance amplifier apparatus of claim 1, wherein the adaptive-loop-gain means adjusts the gains of the amplification stages such that the feedback loop is stable at all overall gains of the transimpedance amplifier apparatus.

9. The transimpedance amplifier apparatus of claim 1, wherein the adaptive-loop-gain means comprises:
 a low pass filter that extracts a signal related to one of the average input-current signal level and average output signal-level; and
 a gain-control block that adjusts the gains of said amplification stages based on the information provided by said signal.

10. The transimpedance amplifier apparatus of claim 1, wherein the feedback network includes an MOS transistor operated in its subthreshold region to provide a logarithmic relationship between the output-voltage signal and the input-current signal.

11. The transimpedance amplifier apparatus of claim 10, wherein the adaptive-loop-gain means uses filtered versions, scaled versions, or shifted versions of the output-voltage signal to adjust the gains of one or more amplifying stages of the transimpedance amplifier apparatus.

12. The transimpedance amplifier apparatus of claim 10 wherein the adaptive-loop-gain means uses filtered versions, scaled versions, or shifted versions of voltages from terminals of the said MOS transistor to adjust the gains of one or more amplifying stages of the transimpedance amplifier apparatus.

13. The transimpedance amplifier apparatus of claim 1, wherein the input-current signal is a photocurrent from at least one of a photodiode, a phototransistor, or a device with means to transduce light to electrons.

14. The transimpedance amplifier apparatus of claim 1, wherein the feedback network contains a unilateralization network for preventing limitations in the bandwidth of the feedback loop and for increasing the speed at which the transimpedance amplifier apparatus performs amplification of the input-current signal.

15. The transimpedance amplifier apparatus of claim 1, wherein the unilateralization network comprises having a transistor having a constant gate voltage with its drain terminal connected to the input of the transimpedance amplifier apparatus and its source terminal connected to remaining circuitry of the feedback network such that neither gate-to-source capacitance nor gate-to-drain capacitance of said transistor causes any feed-through-capacitance limitations in the bandwidth of the transimpedance amplifier apparatus.

16. The transimpedance amplifier apparatus of claim 1, further comprising an input-noise-signal subtraction means for sensing, storing, and subtracting a steady-state background noise portion of the input-current signal, so that only the remaining transient and informative portion of the input-current signal is amplified and transduced to a voltage signal by the transimpedance amplifier apparatus.

17. The transimpedance amplifier apparatus of claim 1, wherein the feedback network contains an exponential conductance element to increase the speed with which the transimpedance amplifier apparatus adjusts to abruptly changing input-current signal levels.

18. A transimpedance amplifier apparatus for providing energy-efficient amplification and feedback conversion of an input-current signal into an output-voltage signal comprising:
 a) a high-gain amplifier connected between an input and an output of the transimpedance amplifier apparatus wherein the high-gain amplifier comprises a cascade of at least three successive lower-gain amplification stages; and
 b) a feedback network connected between the output and input of the transimpedance amplifier apparatus that determines an overall gain from input to output of the transimpedance amplifier apparatus.

19. The transimpedance amplifier apparatus of claim 18, wherein the amplification stages have substantially identical gains to maximize the energy-efficiency of the transimpedance amplifier apparatus.

20. The transimpedance amplifier apparatus of claim 18, wherein the feedback network of the transimpedance amplifier apparatus contains an MOS transistor operated in its subthreshold region to provide a logarithmic relationship between the output-voltage signal and the input-current signal.

21. The transimpedance amplifier apparatus of claim 18, wherein the input-current signal is a photocurrent from at least one of a photodiode, a phototransistor, or a device with a means to transduce light to electrons.

22. The transimpedance amplifier apparatus of claim 18, wherein the feedback network contains a unilateralization network for preventing limitations in the bandwidth of the feedback loop and for increasing the speed at which the transimpedance amplifier apparatus performs amplification of the input-current signal.

23. The transimpedance amplifier apparatus of claim 22, wherein the unilateralization network comprises a transistor having a constant gate voltage with its drain terminal connected to the input of the transimpedance amplifier apparatus and its source terminal connected to remaining circuitry of the feedback network such that neither gate-to-source capacitance nor gate-to-drain capacitance of said transistor cause any feed-through-capacitance limitations in the bandwidth of the transimpedance amplifier apparatus.

24. The transimpedance amplifier apparatus of claim 18, further comprising an input-noise-signal subtraction means for sensing, storing, and subtracting a steady-state background noise portion of the input-current signal, so that only a remaining transient portion of the input-current signal is amplified and transduced to voltage by the transimpedance amplifier apparatus.

25. The transimpedance amplifier apparatus of claim 18, wherein the feedback network contains an exponential conductance element to increase the speed with which the transimpedance amplifier apparatus adjusts to abruptly changing input-current signal levels.

26. A transimpedance amplifier apparatus for providing energy-efficient amplification and feedback conversion of an input-current signal into an output voltage signal comprising:
 a) a high-gain amplifier, connected between an input and an output of the transimpedance amplifier apparatus, comprised of at least one amplification stage; and
 b) a feedback network connected between the input and the output of the transimpedance amplifier apparatus that determines an overall gain from the input to the output of the transimpedance amplifier apparatus; and
 c) an adaptive-loop-gain means for adjusting the amount of amplification provided by the high-gain amplifier based on one of the level of the input-current signal, the level of the output signal, and the gain of said feedback network.

27. The transimpedance amplifier apparatus of claim 26, wherein the adaptive-loop-gain means adjusts the gain of said at least one amplification stage such that an overall bandwidth of the transimpedance amplifier apparatus is substantially constant at all levels of the input-current signal.

28. The transimpedance amplifier apparatus of claim 26, wherein the adaptive-loop-gain means adjusts the gain of said at least one amplification stage such that an overall bandwidth of the transimpedance amplifier apparatus is substantially constant at all gain settings of said feedback network.

29. The transimpedance amplifier apparatus of claim 26, wherein the adaptive-loop-gain means adjusts the gain of said at least one amplification stage such that the overall bandwidth of the transimpedance amplifier apparatus is nearly constant and independent of an overall gain of the transimpedance amplifier apparatus.

30. The transimpedance amplifier apparatus of claim 26, wherein the adaptive-loop-gain means adjusts the gain of said at least one amplification stage such that the feedback loop of the transimpedance amplifier apparatus is stable at all levels of the input-current signal.

31. The transimpedance amplifier apparatus of claim 26, wherein the adaptive-loop-gain means adjusts the gain of said at least one amplification stage such that the feedback loop of the transimpedance amplifier apparatus is stable at all gain settings of said feedback network.

32. The transimpedance amplifier apparatus of claim 26, wherein the adaptive-loop-gain means adjusts the gains of said at least one amplification stage such that the feedback loop is stable at all overall gains of the transimpedance amplifier apparatus.

33. The transimpedance amplifier apparatus of claim 26, wherein the adaptive-loop-gain means comprises:
a low pass filter that extracts a signal related to one of an average input-current signal level and an average output signal-level; and
a gain-control block that adjusts the gain of said at least one amplification stage based on the information provided by said signal.

34. The transimpedance amplifier apparatus of claim 26, wherein the feedback network contains an MOS transistor operated in its subthreshold region to provide a logarithmic relationship between the output-voltage signal and the input-current signal.

35. The transimpedance amplifier apparatus of claim 34, wherein the adaptive-loop-gain means uses filtered versions, scaled versions, or shifted versions of voltages from terminals of said MOS transistor to adjust the gain of said at least one amplification stage of the transimpedance amplifier apparatus.

36. The transimpedance amplifier apparatus of claim 34, wherein the adaptive-loop-gain means uses filtered versions, scaled versions, or shifted versions of the logarithmic output-voltage signal to adjust the gain of said at least one amplification stage of the transimpedance amplifier apparatus.

37. The transimpedance amplifier apparatus of claim 26, wherein the input-current signal is a photocurrent from at least one of a photodiode, a phototransistor, or a device with a means to transduce light to electrons.

38. The transimpedance amplifier apparatus of claim 26, wherein the feedback network contains a unilateralization network for preventing limitations in the bandwidth of the feedback loop and for increasing the speed at which the transimpedance amplifier apparatus performs amplification of the input-current signal.

39. The transimpedance amplifier apparatus of claim 38, wherein the unilateralization network comprises a transistor having a constant gate voltage with its drain terminal connected to the input of the transimpedance amplifier apparatus and with its source terminal connected to the remaining circuitry of the feedback network such that neither gate-to-source capacitance nor gate-to-drain capacitance of said transistor causes any feed-through-capacitance limitations in the bandwidth of the transimpedance amplifier apparatus.

40. The transimpedance amplifier apparatus of claim 26, further comprising an input-noise-signal subtraction means for sensing, storing, and subtracting a steady-state background noise portion of the input-current signal, so that only the remaining transient and informative portion of the input-current signal is amplified and transduced to the output-voltage signal by the transimpedance amplifier apparatus.

41. The transimpedance amplifier apparatus of claim 26, wherein the feedback network contains an exponential conductance element to increase a speed with which the transimpedance amplifier apparatus adjusts to abruptly changing levels of the input-current signal.

42. An energy-efficient photoreceptor apparatus for measuring components of blood in a specimen, comprising:
a) a plurality of light emitting devices for emitting light of at least two predetermined spectral wavelengths to illuminate a site on a specimen containing blood;
b) at least one photodiode for receiving a portion of said light transmitted or reflected by the illuminated site and producing at least one photocurrent signal; and
c) the transimpedance amplifier apparatus of any one of claims 1, 18, and 26 for converting said at least one photocurrent signal to at least one output-voltage signal that is input to a processing unit wherein the processing unit processes said at least one output-voltage signal from the transimpedance amplifier apparatus so that a component of blood may be measured.

43. The energy-efficient photoreceptor apparatus of claim 42, wherein the power allocated to said plurality of light emitting devices and said transimpedance amplifier apparatus is optimized such that the sum of the power level dissipated in the plurality of light emitting devices and the power dissipated in the transimpedance amplifier apparatus is substantially minimized.

44. The energy-efficient photoreceptor apparatus of claim 42, wherein the power allocated to said plurality of light emitting devices, said transimpedance amplifier apparatus, and the processing unit is optimized such that the sum of the power dissipated in said plurality of light emitting devices, the power dissipated in said transimpedance amplifier apparatus, and the power dissipated in the processing unit is substantially minimized.

45. The energy-efficient photoreceptor apparatus of claim 42, further comprising a means for adapting the power consumed by said plurality of light emitting devices to the specimen, so that the energy consumed by said plurality of light emitting devices varies based on the level of said at least one photocurrent signal.

46. The energy-efficient photoreceptor apparatus of claim 42, wherein the processing unit further comprises an analog-processing block to reduce the power consumption of the photoreceptor apparatus.

47. The energy-efficient photoreceptor apparatus of claim 46, wherein the analog-processing block contains at least one envelope-detection circuit for measuring the amplitudes of signals.

48. The energy-efficient photoreceptor apparatus of claim 46, wherein the analog-processing block contains a ratio-computation block for computing a ratio of a first output-voltage signal corresponding to a first photocurrent signal from a first illumination of one of said plurality of light emitting devices at a first predetermined spectral wavelength and a second output-voltage signal corresponding to a second photocurrent signal from a second illumination of one of said plurality of light emitting devices at a second predetermined spectral wavelength.

49. The energy-efficient photoreceptor apparatus of claim 48, wherein the ratio-computation block further comprises output signal limiting circuitry.

50. The energy-efficient photoreceptor apparatus of claim 42, wherein the processing unit further comprises analog-to-digital conversion circuitry for converting an analog output-voltage signal into a digital output-voltage signal.

51. The energy-efficient photoreceptor apparatus of claim 42, further comprising a communication unit including a wireless transmission means for wirelessly transmitting at least one signal from the processing unit to a receiving unit at a location remote from the photoreceptor apparatus.

52. An energy-efficient apparatus for measuring components of blood in a specimen, comprising:

a) a plurality of light emitting devices for emitting light of at least two predetermined spectral wavelengths to illuminate a site on a specimen containing blood;
b) at least one photodiode for receiving a portion of said light transmitted or reflected by the illuminated site and producing at least one photocurrent signal; and
c) the transimpedance amplifier apparatus of any one of claims 1, 18, and 26 for converting said at least one photocurrent signal to at least one output-voltage signal, wherein said at least one output-voltage signal of the transimpedance amplifier apparatus serves as input to a communication unit including a wireless transmitting means for wirelessly transmitting said at least one output-voltage signal to a receiving unit at a location remote from the location of said energy-efficient apparatus.

53. The energy-efficient apparatus of claim 52, wherein the receiving unit contains a display unit for displaying information transmitted from the energy-efficient apparatus.

* * * * *